US006022864A

United States Patent [19]
Li et al.

[11] Patent Number: 6,022,864
[45] Date of Patent: *Feb. 8, 2000

[54] NUCLEIC ACID RESPIRATORY SYNCYTIAL VIRUS VACCINES

[75] Inventors: Xiaomao Li, Thornhill; Mary E. Ewasyshyn, Willowdale; Suryaprakash Sambhara, Markham; Michel H. Klein, Willowdale, all of Canada

[73] Assignee: Connaught Laboratories Limited, North York, Canada

[ * ] Notice: This patent is subject to a terminal disclaimer.

[21] Appl. No.: 08/973,720

[22] PCT Filed: Jun. 7, 1996

[86] PCT No.: PCT/CA96/00398

§ 371 Date: Mar. 27, 1998

§ 102(e) Date: Mar. 27, 1998

[87] PCT Pub. No.: WO96/40945

PCT Pub. Date: Dec. 19, 1996

Related U.S. Application Data

[63] Continuation-in-part of application No. 08/476,397, Jun. 7, 1995.

[51] Int. Cl.[7] ........................ A61K 31/70; A61K 39/155; C12N 15/64; C12P 21/02

[52] U.S. Cl. ........................ 514/44; 424/211.1; 435/69.3; 435/91.4; 435/320.1

[58] Field of Search ........................ 424/211.1; 435/69.1, 435/69.3, 91.4, 320.1; 514/44

[56] References Cited

U.S. PATENT DOCUMENTS 5,589,466 12/1996 Felgner et al. ............................ 514/44

OTHER PUBLICATIONS

Tang et al. (1993) High–level and erythroid–specific expression of human glucose–6–phosphate dehydrogenase in transgenic mice. J. Biol. Chem. 268:9522–9525, May 1993.

Wathan et al. (1989) Immunization of cotton rats with the human respiratory syncytial virus F glycoprotein produced using a baculovirus vector. J. Infect. Dis. 159:255–264, Feb. 1989.

Wertz et al. (1987) Expression of the fusion protein of human respiratory syncytial virus from recombinant vaccinia virus vectors and protection of vaccinated mice. J. Virol. 61:293–301, Feb. 1987.

Collis et al. (1990) Definition of the minimal requirements within the human beta–globin gene and the dominant control region for high level expression. EMBO J. 9:233–240, Jan. 1990.

*Primary Examiner*—Nancy Degen
*Assistant Examiner*—Robert Schwartzman
*Attorney, Agent, or Firm*—Sim & McBurney

[57] ABSTRACT

Vectors containing a nucleotide sequence coding for an F protein of respiratory syncytial virus (RSV) and a promoter for such sequence, preferably a cytomegalovirus promoter, are described. Such vectors also may contain a further nucleotide sequence located adjacent to the RSV F protein enclosing sequence to enhance the immunoprotective ability of the RSV F protein when expressed in vivo. Such vectors may be used to immunize a host, including a human host, by administration thereto. Such vectors also may be used to produce antibodies for detection of RSV infection in a sample.

44 Claims, 27 Drawing Sheets

RESTRICTION MAP OF THE RSV F GENE

5' — AccI — EarI — PpuMI — (500) — BclI — MamI — (1000) — NlaIV — NsiI — (1500) — BspHI — 3' bp

FIG. 1

FIG. 2A.   NUCLEOTIDE SEQUENCE OF THE RSV F GENE.

```
                            ←——————— SP ———————→
    MET GLU LEU PRO ILE LEU LYS ALA ASN ALA ILE THR THR ILE LEU ALA ALA VAL THR PHE
5'  ATGGAGTTGCCAATCCTCAAAGCAAATGCAATTACCACAATCCTGCTGCAGTCACATTT
    TACCTCAACGGTTAGGAGTTTCGTTTACGTTAATGGTGTTAGGACGACGTCAGTGTAAA
             10        20        30        40        50        60

CYS PHE ALA SER SER GLN ASN ILE THR GLU GLU PHE TYR GLN SER THR CYS SER ALA VAL
    TGCTTTGCTTCTAGTCAAAACATCACTGAAGAATTTTATCAATCAACATGCAGTGCAGTT
    ACGAAACGAAGATCAGTTTGTAGTGACTTCTTAAAATAGTTAGTTGTACGTCACGTCAA
             70        80        90       100       110       120

SER LYS GLY TYR LEU SER ALA LEU ARG THR GLY TRP TYR THR SER VAL ILE THR ILE GLU
    AGCAAAGGCTATCTTAGTGCTCTAAGAACTGGTTGGTATACTAGTGTTATAACTATAGAA
    TCGTTTCCGATAGAATCACGAGATTCTTGACCAACCATATGATCACAATATTGATATCTT
            130       140       150       160       170       180

LEU SER ASN ILE LYS GLU ASN LYS CYS ASN GLY THR ASP ALA LYS VAL LYS LEU MET LYS
    TTAAGTAATATCAAGGAAAATAAGTGTAATGGAACAGATGCTAAGGTAAAATTGATGAAA
    AATTCATTATAGTTCCTTTATTCACATTACCTTGTCTACGATTCCATTTTAACTACTTT
            190       200       210       220       230       240

GLN GLU LEU ASP LYS TYR LYS ASN ALA VAL THR GLU LEU GLN LEU LEU MET GLN SER THR
    CAAGAATTAGATAAATATAAAAATGCTGTAACAGAATTGCAGTTGCTCATGCAAAGCACA
    GTTCTTAATCTATTTATATTTTTACGACATTGTCTTAACGTCAACGAGTACGTTTCGTGT
            250       260       270       280       290       300

PRO ALA ALA ASN ASN ARG ALA ARG ARG GLU LEU PRO ARG PHE MET ASN TYR THR LEU ASN
    CCAGCAGCAAACAATGAGCCAGAAGAACTACCAAGGTTTATGAATTATACACTCAAC
    GGTCGTCGTTTGTTACTCGGTCTTCTTGATGGTTCCAAATACTTAATATGTGAGTTG
            310       320       330       340       350       360
```

FIG.2B.

```
                                                                    F2-F1CLEAVAGE SITE
ASN THR LYS LYS THR ASN VAL THR LEU SER LYS LYS ARG LYS ARG↓PHE LEU GLY PHE
AATACCAAAAAAACCAATGTAACATTAAGCAAGAAAAGAAAAaAAGATTCTTGGTTT
TTATGGTTTTTTGGTTACATTGTAATTCGTTCTTTCCTTTCTTCTAAAGAACCAAAA
         370       380       390       400       410       420

LEU LEU GLY VAL GLY SER ALA ILE ALA SER GLY ILE ALA VAL SER LYS VAL LEU HIS LEU
TTGTTAGGTGTTGGATCTGCAATCGCCAGTGGCATTGCTGTATCTAAGGTCCTGCACTTA
AACAATCCACAACCTAGACGTTAGCGGTCACCGTAACGACATAGATTCCAGGACGTGAAT
         430       440       450       460       470       480

GLU GLY VAL ASN LYS ILE LYS SER ALA LEU LEU SER THR ASN LYS SER ALA VAL VAL SER
GAAGGAGAAGTGAACAAGATCAAAAGTGCTCTACTATCCACAAACAAGTCTGCTAGTCAGC
CTTCCTCTTCACTTGTTCTAGTTTTCACGAGATGATAGGTGTTTGTTCCGGCATCAGTCG
         490       500       510       520       530       540

LEU SER ASN GLY VAL SER VAL LEU THR SER LYS VAL LEU ASP LEU LYS ASN TYR ILE ASP
TTATCAAATGGAGTTAGTGTCTTAACCAGCAAAGTGTTAGACCTCAAAAACTATATAGAT
AATAGTTTACCTCAATCACAGAATTGGTCGTTTCACAATCTGGAGTTTTGATATATCTA
         550       560       570       580       590       600

LYS GLN LEU LEU PRO ILE VAL ASN LYS GLN SER CYS ARG ILE SER ASN ILE GLU THR VAL
AAACAATTGTTACCTATTGTGAATAAGCAAAGCTGCAGAATATCAAATATCAAATAGAAACTGTG
TTTGTTAACAATGGATAACACTTATTCGTTTCGACGTCTTATAGTTTATATCTTTGACAC
         610       620       630       640       650       660

ILE GLU PHE GLN HIS LYS ASN ASN ARG LEU LEU GLU ILE THR ARG GLU PHE SER VAL ASN
ATAGAGTTCCAACAAAAGAACAACAGACTACTAGAGATTACCAGGGAATTAGTGTTAAT
TATCTCAAGGTTGTTTTCTTGTTGTCTGATGATCTCTAATGGTCCCTTAAATCACAATTA
         670       680       690       700       710       720

ALA GLY VAL THR THR PRO VAL SER THR TYR MET LEU THR ASN SER GLU LEU LEU SER LEU
GCAGGTGTAACTACACCTGTAAGCACTTACATGTTAACTAATAGTGAATTATTGTCATTA
CGTCCACATTGATGTGGACATTCGTGAATTACAATGTACAATTATCACTTAATAACAGTAAT
         730       740       750       760       770       780
```

FIG.2C.

```
ILE ASN ASP MET PRO ILE THR ASN ASP GLN LYS LYS LEU MET SER ASN ASN VAL GLN ILE
ATCAATGATATGCCTATAACAAATGATCAGAAAAAGTTAATGTCCAACAATGTTCAAATA
TAGTTACTATACGGATATTGTTTACTAGTCTTTTCAATTACAGGTTGTTACAAGTTAT
         790       800       810       820       830       840

VAL ARG GLN GLN SER TYR SER ILE MET SER ILE ILE LYS GLU GLU VAL LEU ALA TYR VAL
GTTAGACAGCAAAGTTACTCTATCATGTCCATAATAAAAGAGGAAGTCTTAGCATATGTA
CAATCTGTCGTTTCAATGAGATAGTACAGGTATTATTTTCTCCTTCAGAATCGTATACAT
         850       860       870       880       890       900

VAL GLN LEU PRO LEU TYR GLY VAL ILE ASP THR PRO CYS TRP LYS LEU HIS THR SER PRO
GTACAATTACCACTATATGGTGTGATAGATACACCTTGTTGGAAATTACACACATCCCT
CATGTTAATGGTGATATACCACACTATCTATGTGGAACAACCTTTAATGTGTAGGGGA
         910       920       930       940       950       960

LEU CYS THR THR ASN THR LYS GLU GLY SER ASN ILE CYS LEU THR ARG THR ASP ARG GLY
CTATGTACAACAACAAACACAAAGAAGGTCAAACATCTGTTAACAAGAACTGACAGAGGA
GATACATGTTGTTGTTGTTTCTTCCAGTTGTAGACAAATTGTTCTTGACTGTCTCCT
         970       980       990      1000      1010      1020

TRP TYR CYS ASP ASN ALA GLY SER VAL SER PHE PHE PRO GLN ALA GLU VAL THR CYS LYS VAL
TGGTACTGTGACAATGCAGGATCAGTATCTTTCTTCCCACAAGCTGAAACATGTAAAGTT
ACCATGACACTGTTACGTCCTAGTCATAGAAAGAAGGGGTGTTCGACTTTGTACATTCAA
        1030      1040      1050      1060      1070      1080

GLN SER ASN ARG VAL PHE CYS ASP THR MET ASN SER LEU THR LEU PRO SER GLU VAL ASN
CAATCGAATCGAGTGTATTTGTGACACAATGAACAGTTAACATTACCAAGTGAAGTAAAT
GTTAGCTTAGCTCATAAAACACTGTTACTTGTCAATTGTAATGGTTCACTTCATTTA
        1090      1100      1110      1120      1130      1140

LEU CYS ASN VAL ASP ILE PHE ASN PRO LYS TYR ASP CYS LYS ILE MET THR SER LYS THR
CTCTGCAAGTTGACATATTCAATCCAAATATGATTGTAAATTATGACTTCAAAAACA
GAGACGTTCAACTGTATAAGTTAGGTTTATACTAACATTTAATACTGAAGTTTGT
        1150      1160      1170      1180      1190      1200
```

```
ASP VAL SER SER SER VAL ILE THR SER LEU GLY ALA ILE VAL SER CYS TYR GLY LYS THR
GATGTAAGCAGCTCCGTTATCACATCTCTAGGAGCCATTGTGTCATGCTATGGCAAAACT
CTACATTCGTCGAGGCAATAGTGTAGAGATCCTCGGTAACACAGTACGATACCGTTTTGA
                  1210              1220              1230              1240              1250              1260

LYS CYS THR ALA SER ASN LYS ASN ARG GLY ILE ILE LYS THR PHE SER ASN GLY CYS ASP
AAATGTACAGCAGCATCCAATAAAAATCGTGGAATCATAAAGACATTTCTAACGGGTGAT
TTTACATGTCGTAGGTTATTTTTAGCACCTTAGTATTTCTGTAAAAGATTGCCCACACTA
                  1270              1280              1290              1300              1310              1320

TYR VAL SER ASN LYS GLY VAL ASP THR VAL SER VAL GLY ASN THR LEU TYR TYR VAL ASN
TATGTATCAAATAAAGGGGTGGACACTGTGTCTGTAGGTAACACATTATATTATGTAAAT
ATACATAGTTTATTTCCCCACCTGTGACACAGATCCATTGTGTAATATAATACATTTA
                  1330              1340              1350              1360              1370              1380

LYS GLN GLU GLY LYS SER LEU TYR VAL LYS GLY GLU PRO ILE ILE ASN PHE TYR ASP PRO
AAGCAAGAAGGCAAAAGTCTCTATGTAAAAGGTGAACCAATAATAAATTTCTATGACCCA
TTCGTTCTTCCGTTTTCAGAGATACATTTTCCACTTGGTTATTATTTAAAGATACTGGGT
                  1390              1400              1410              1420              1430              1440

LEU VAL PHE PRO SER ASP GLU PHE ASP ALA SER ILE SER GLN VAL ASN GLU LYS ILE ASN
TTAGTATTCCCCTCTGATGAATTTGATGCATCAATATCTCAAGTCAATGAGAAGATTAAC
AATCATAAGGGGAGACTACTTAAACTACGTAGTTATAGAGTTCAGTTACTCTTCTAATTG
                  1450              1460              1470              1480              1490              1500

GLN SER LEU ALA PHE ILE ARG LYS SER ASP GLU LEU LEU HIS ASN VAL ASN ALA GLY LYS
CAGAGTTTAGCATTTATTCGTAAATCCGATGAATTATTACATAATGTAAATGCTGGTAAA
GTCTCAAATCGTAAATAAGCATTTAGGCTACTTAATAATGTATTACATTTACGACCATTT
                  1510              1520              1530              1540              1550              1560

SER THR THR ASN ILE MET ILE THR THR ILE ILE GLU ILE ILE VAL ILE LEU LEU SER
TCAACCACAAATATCATGATAACTACTATAATTATAGAATTATAGTAATTGTTATCA
AGTTGGTGTTTTATAGTACTATTGATGATATTAATATTCTAATATCATTATAACAATAGT
                  1570              1580              1590              1600              1610              1620
                                                      ────────── TM ──────────▶
```

FIG. 2D.

```
LEU ILE ALA VAL GLY LEU LEU LEU TYR CYS LYS ALA ARG SER THR PRO VAL THR LEU SER
TTAATTGCTGTTGGACTGCTCCTATACTGTAAGGCCAGAAGCACCAGTCACACTAAGC
AATTAACGACAACCTGACGAGGATATGACATTCCGGTCTTCGTGGTCAGTGTGATTCG
         1630              1640              1650              1660              1670              1680

LYS, ASP GLN LEU SER GLY ILE ASN ASN ILE ALA PHE SER ASN
AAGGATCAACTGAGTGGTATAAATAATTGCATTTAGTAACTGAATAAAAAATAGCACCT
TTCCTAGTTGACTCACCATATTTATTAACGTAAATCATTGACTTATTTTTATCGTGGA
         1690              1700              1710              1720              1730              1740

AATCATGTTCTTACAAATGGTTTACTATCTGCTCATAGACAACCCATCTATCATTGGATTT
TTAGTACAAGAATGTTTACCAAATGATAGACGAGTATCTGTTGGGTAGATAGTAACCTAAA
         1750              1760              1770              1780              1790              1800

TCTTAAAATCTGAACTTCATCGAAACTCTTATCTTATAAACCATCTCTCACTTACACTATTTA
AGAATTTTAGACTTGAAGTAGCTTTGAGAATAGAATATTTGGTAGAATGTGATAAAT
         1810              1820              1830              1840              1850              1860

AGTAGATTCCTAGTTTATATAGTTATAT 3'
TCATCTAAGGATCAAATATCAATATA
         1870              1880
```

NUCLEOTIDE SEQUENCE OF THE RSV F GENE.

← SP →

5'
MET GLU LEU PRO ILE LEU LYS ALA ASN ALA ILE THR THR ILE LEU ALA ALA VAL THR PHE
ATGGAGTTGCCAATCCTCAAAGCAAATGCAATTACCACAATCCTCGCTGCAGTCACATTT
TACCTCAACGGTTAGGAGTTTCGTTTACGTTAATGGTGTTAGGAGCGACGTCAGTGTAAA
          10        20        30        40        50        60

CYS PHE ALA SER SER GLN ASN ILE THR GLU GLU PHE TYR GLN SER THR CYS SER ALA VAL
TGCTTTGCTTCTAGTCAAAACATCACTGAAGAATTTTATCAACATCAACATGCAGTT
ACGAAACGAAGATCAGTTTTGTAGTGACTTCTTAAAATAGTTGTACGTCACGTCAA
          70        80        90       100       110       120

SER LYS GLY TYR LEU SER ALA LEU ARG THR GLY TRP TYR THR SER VAL ILE THR ILE GLU
AGCAAAGGCTATCTTAGTGCTCTAAGAACTGGTTGGTATACTAGTGTTATAACTATAGAA
TCGTTTCCGATAGAATCACGAGATTCTTGACCAACCATAGTCACAATATTGATATCTT
         130       140       150       160       170       180

LEU SER ASN ILE LYS GLU ASN LYS CYS ASN GLY THR ASP ALA LYS VAL LYS LEU MET LYS
TTAAGTAATATCAAGGAAAATAAGTGTAATGGAACAGATGCTAAGGTAAAATTGATGAAA
AATTCATTATAGTTCCTTTATTCACATTACCTTGTCTACGATTCCATTTTAACTACTTT
         190       200       210       220       230       240

GLN GLU LEU ASP LYS TYR LYS ASN ALA VAL THR GLU LEU GLN LEU LEU MET GLN SER THR
CAAGAATTAGATAAATATAAAAATGCTGTAACAGAATTGCAGTTGCTCATGCAAAGCACA
GTTCTTAATCTATTTATATTTTTACGACATTGTCTTAACGTCAACGAGTACGTTTCGTGT
         250       260       270       280       290       300

PRO ALA ALA ASN ASN ARG ALA ARG ARG GLU LEU PRO ARG PHE MET ASN TYR THR LEU ASN
CCAGCAGCAAACAATCGAGCCAGAAGAGAACTACCAAGGTTTATGAATTATACACTCAAC
GGTCGTCGTTTGTTAGCTCGGTCTTCTCTTGATGGTTCCAAATACTTAATATGTGAGTTG
         310       320       330       340       350       360

FIG.3B.

```
                                                                F2-F1CLEAVAGE SITE
ASN THR LYS LYS THR ASN VAL THR LEU SER LYS LYS ARG LYS ARG ARG↓PHE LEU GLY PHE
AATACCAAAAGAACCAATGTAACATTGTAACATTAAGCAAGAAAAGAAAAGAAAAGATTTCTTGTTTT
TTATGGTTTTTTTGGTTACATTGTAATTCGTTCCTTTCTTTCTTTCTAAAGAACCAAAA
        370           380           390           400           410           420

LEU LEU GLY VAL GLY SER ALA ILE ALA SER GLY ILE ALA VAL SER LYS VAL LEU HIS LEU
TTGTTAGGTGTTGGATCTGCAATCGCCAGTGGCATTGCTGTATCTAAGTCCTGCACTTA
AACAATCCACAACCTAGACGTTAGCGGTCACCGTAACGACATAGATTCCAGGACGTGAAT
        430           440           450           460           470           480

GLU GLY VAL ASN LYS ILE LYS SER ALA LEU LEU SER THR ASN LYS ALA VAL VAL SER
GAAGGAGAAGTGAACAAGATCAAAAGTGCTCTACTATCCACAAACAAGCCGTAGTCAGC
CTTCCTCTTCACTTGTTCTAGTTTTCACGAGATGATAGGTGTTGTTCGGCATCAGTCG
        490           500           510           520           530           540

LEU SER ASN GLY VAL SER VAL LEU THR SER LYS VAL LEU ASP LEU LYS ASN TYR ILE ASP
TTATCAAATGGAGTTAGTGTCTTAACCAGCAAAGTGTTAGACCTCAAAAACTATATAGAT
AATAGTTTACCTCAATCACAGAATTGGTCGTTTCACATCTGGAGTTTTGATATATCTA
        550           560           570           580           590           600

LYS GLN LEU PRO ILE VAL ASN LYS GLN SER CYS ARG ILE SER ASN ILE GLU THR VAL
AAACAATTGTTACCTATTGTGAATAAGCAAAGCTGCAGAATATCAAATATAGAAACTGTG
TTTGTTAACAATGGATAACACTTATTCGTTTCGACGTCTTATAGTTTATATCTTTGACAC
        610           620           630           640           650           660

ILE GLU PHE GLN HIS LYS ASN ASN ARG LEU LEU GLU ILE THR ARG GLU PHE SER VAL ASN
ATAGAGTTCCAACAAAAGAACAACAGACTACTAGAGATTACCAGGAATTAGTGTAAT
TATCTCAAGGTTGTTTTCTTGTTGTCTGATGATCTCTAATGGTCCCTTAATCACAATTA
        670           680           690           700           710           720

ALA GLY VAL THR THR PRO VAL SER THR TYR MET LEU THR ASN SER GLU LEU LEU SER LEU
GCAGGTGTAACTACACCTGTAAGCACTTACATGTTAACTAATAGTGAATTATTGTCATTA
CGTCCACATTGATGTGGACATTCGTGAATGTACAATTGATTATCACTTAATAACAGTAAT
        730           740           750           760           770           780
```

FIG.3C.

```
ILE ASN ASP MET PRO ILE THR ASN ASP GLN LYS LYS LEU MET SER ASN ASN VAL GLN ILE
ATCAATGATATGCCTATAACAAATGATCAGAAAAAGTTAATGTCCAACAATGTTCAAATA
TAGTTACTATACGGATATTGTTTACTAGTCTTTTCAATTACAGTTGTTACAAGTTTAT
        790        800        810        820        830        840

VAL ARG GLN GLN SER TYR SER ILE MET SER ILE ILE LYS GLU GLU VAL VAL LEU ALA TYR VAL
GTTAGACAGCAAAGTTACTCTATCATGTCCATAATAAAAGAGGAAGTCTTAGCATATGTA
CAATCTGTCGTTTCAATGAGATAGTACAGGTATTATTTTCTCCTTCAGAATCGTATACAT
        850        860        870        880        890        900

VAL GLN LEU PRO LEU TYR GLY VAL ILE ASP THR PRO CYS TRP LYS LEU HIS THR SER PRO
GTACAATTACCACTATATGGTGTGATAGATACACCTTGTTGGAAATTACACACATCCCT
CATGTTAATGGTGATATACCACACTATCTATGTGGAACAACCTTTAATGTGTAGGGGA
        910        920        930        940        950        960

LEU CYS THR THR ASN THR LYS GLU GLY SER ASN ILE CYS LEU THR ARG THR ASP ARG GLY
CTATGTACAACCAACACAAAGAAGGGTCAAACATCTGTTTAACAAGAACTGACAGAGGA
GATACATGTTGGTTGTGTTTCTTCCCAGTTTGTAGACAAATGTTCTTGACTGTCTCCT
        970        980        990        1000       1010       1020

TRP TYR CYS ASP ASN ALA GLY SER VAL SER PHE PHE PRO GLN ALA GLU THR CYS LYS VAL
TGGTACTGTGTGACAATGCAGGATCAGTCAGTATCTTTCTTCCCACAAGCTGAAACATGTAAAGTT
ACCATGACACTGTTACGTCCTAGTCAGTCATAGAAAGAAGGGTGTTCGACTTTGTACATTTCAA
        1030       1040       1050       1060       1070       1080

GLN SER ASN ARG VAL PHE CYS ASP THR MET ASN SER LEU THR LEU PRO SER GLU VAL ASN
CAATCGAATCGAGTTGTTTGTGACACATGAACAGTTTAACATTACCAAGTGAAGTAAAT
GTTAGCTTAGCTCATCAAACACTGTGTTACTTGTCAAATTGTAATGGTTCACTTCATTTA
        1090       1100       1110       1120       1130       1140

LEU CYS ASN VAL ASP ILE PHE ASN PRO LYS TYR ASP CYS LYS ILE MET THR SER LYS THR
CTCTGCAATGTTGACATATTCAATCCCAAATATGATTGTAAAATTATGACTTCAAAACA
GAGACGTTACAACTGTATAAGTTAGGGTTTATACTAACATTTTAATACTGAAGTTTTGT
        1150       1160       1170       1180       1190       1200
```

FIG.3D.

```
ASP VAL SER SER VAL ILE THR SER LEU GLY ALA ILE VAL SER CYS TYR GLY LYS THR
GATGTAAGCAGCTCCGTTATCACATCTCTAGGAGCCATTGTGTCATGTTATGGCTATGGCAAAACT
CTACATTCGTCGAGGCAATAGTGTAGAGATCCTCGGTAACACAGTACGATACCGTTTTGA
     1210      1220      1230      1240      1250      1260

LYS CYS THR ALA SER ASN LYS ASN ARG GLY ILE ILE LYS THR PHE SER ASN GLY CYS ASP
AAATGTACAGCATCCAATAAAAATCGTGGAATCATAAAGACATTTCTAACGGGTGTGAT
TTTACATGTCGTAGTTATTTTAGCACCTTAGTATTTCTGTAAAAGATTGCCCACACTA
     1270      1280      1290      1300      1310      1320

TYR VAL SER ASN LYS GLY VAL ASP THR VAL SER VAL GLY ASN THR LEU TYR TYR VAL ASN
TATGTATCAAATAAAGGGGTGGACACTGTGTCTGTAGGTAACACATTATATTATGTAAAT
ATACATAGTTTATTTCCCCACCTGTGACACAGAGACATCCATTGTGTAATATAATACATTTA
     1330      1340      1350      1360      1370      1380

LYS GLU GLY LYS TYR VAL LYS GLY GLU PRO ILE ILE ASN PHE TYR ASP PRO
AAGCAAGAAGGCAAAAGTCTCTATGTAAAAGGTGAACCAATAAJAAATTTCTATGACCCA
TTCGTTCTTCCGTTTTCAGAGATACATTTTCCACTTGGTTATTATTTAAAGATACTGGGT
     1390      1400      1410      1420      1430      1440

LEU VAL PHE PRO SER ASP GLU PHE ASP ALA SER ILE SER GLN VAL ASN GLU LYS ILE ASN
TTAGTATTCCCCTCTGATGAATTTGATGCATCAATATCTCAAGTCAATGAGAAGATTAAC
AATCATAAGGGGAGACTACTTAAACTACGTAGTTATAGAGTTCAGTTACTCTTCTAATTG
     1450      1460      1470      1480      1490      1500

GLN SER LEU ALA PHE ILE ARG LYS SER ASP GLU LEU LEU HIS ASN VAL ASN ALA GLY LYS
CAGAGTTTAGCATTTATTCGTAAATCCGATGAATTATTACATAATGTAAATGCTGGTAAA
GTCTCAAATCGTAAATAAGCATTTAGGCTACTTAATAATGTATTACATTTACGACCATTT
     1510      1520      1530      1540      1550      1560

SER THR THR ASN ILE MET Thr Stop Stop Stop Bam HI
TCAACCACAAATATCATGACTTGATAATGAGGATCC
AGTTGGTGTTTATAGTACTGAACTATTACTCCTAGG
     1570
```

FIG.8

```
401  TTGGGACCC  TTGATTGTTC  TTTCTTTTTC  GCTATTGTAA  AATTCATGTT
451  ATATGGAGGG  GGCAAAGTTT  TCAGGGTGTT  GTTTAGAATG  GGAAGATGTC
501  CCTTGTATCA  CCATGGACCC  TCATGATAAT  TTGTTTCTT.  TCACTTTCTA
551  CTCTGTTGAC  AACCATTGTC  TCCTCTTATT  TTCTTTTCAT  TTTCTGTAAC
601  TTTTCGTTA   AACTTTAGCT  TGCATTTGTA  ACGAATTTTT  AAATTCACTT
651  TGTTTATTT   GTCAGATTGT  AAGTACTTTC  TCTAATCACT  TTTTTTTCAA
701  GGCAATCAGG  GTATATTATA  TTGTACTTCA  GCACAGTTTT  AGAGAACAAT
751  TGTTATAATT  AAATGATAAG  GTAGAATATT  TCTGCATATA  AATTCTGGCT
801  GGCGTGGAAA  TATTCTTATT  GGTAGAAACA  ACTACATCCT  GGTCATCATC
851  CTGCCTTTCT  CTTTATGGTT  ACAATGATAT  ACACTGTTTG  AGATGAGGAT
901  AAAATACTCT  GAGTCCAAAC  CGGGCCCCTC  TGCTAACCAT  GTTCATGCCT
951  TCTTCTTTTT  CCTACAG                             GTGAGT
```

NUCLEIC ACID RESPIRATORY SYNCYTIAL VIRUS VACCINES

REFERENCE TO RELATED APPLICATION

This application is a United States National Phase Application under 35 USC 371 of PCT/CA96/00398 filed Jun. 7, 1996, which is a continuation-in-part of copending U.S. patent application Ser. No. 08/476,397, filed Jun. 7, 1995.

FIELD OF INVENTION

The present invention is related to the field of Respiratory Syncytial Virus (RSV) vaccines and is particularly concerned with vaccines comprising nucleic acid sequences encoding the fusion (F) protein of RSV.

BACKGROUND OF INVENTION

Respiratory syncytial virus (RSV), a negative-strand RNA virus belonging to the Paramyxoviridae family of viruses, is the major viral pathogen responsible for bronchiolitis and pneumonia in infants and young children (ref. 1—Throughout this application, various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure). Acute respiratory tract infections caused by RSV result in approximately 90,000 hospitalizations and 4,500 deaths per year in the United States (ref. 2). Medical care costs due to RSV infection are greater than $340M annually in the United States alone (ref. 3). There is currently no licensed vaccine against RSV. The main approaches for developing an RSV vaccine have included inactivated virus, live-attenuated viruses and subunit vaccines.

The F protein of RSV is considered to be one of the most important protective antigens of the virus. There is a significant similarity (89% identity) in the amino acid sequences of the F proteins from RSV subgroups A and B (ref. 3) and anti-F antibodies can cross-neutralize viruses of both subgroups as well as protect immunized animals against infection with viruses from both subgroups (ref. 4). Furthermore, the F protein has been identified as a major target for RSV-specific cytotoxic T-lymphocytes in mice and humans (ref. 3 and ref. 5).

The use of RSV proteins as vaccines may have obstacles. Parenterally administered vaccine candidates have so far proven to be poorly immunogenic with regard to the induction of neutralizing antibodies in seronegative humans or chimpanzees. The serum antibody response induced by these antigens may be further diminished in the presence of passively acquired antibodies, such as the transplacentally acquired maternal antibodies which most young infants possess. A subunit vaccine candidate for RSV consisting of purified fusion glycoprotein from RSV infected cell cultures and purified by immunoaffinity or ion-exchange chromatography has been described (ref. 6). Parenteral immunization of seronegative or seropositive chimpanzees with this preparation was performed and three doses of 50 µg were required in seronegative animals to induce an RSV serum neutralizing titre of approximately 1:50. Upon subsequent challenge of these animals with wild-type RSV, no effect of immunization on virus shedding or clinical disease could be detected in the upper respiratory tract. The effect of immunization with this vaccine on virus shedding in the lower respiratory tract was not investigated, although this is the site where the serum antibody induced by parenteral immunization may be expected to have its greatest effect. Safety and immunogenicity studies have been performed in a small number of seropositive individuals. The vaccine was found to be safe in seropositive children and in three seronegative children (all >2.4 years of age). The effects of immunization on lower respiratory tract disease could not be determined because of the small number of children immunized. One immunizing dose in seropositive children induced a 4-fold increase in virus neutralizing antibody titres in 40 to 60% of the vaccinees. Thus, insufficient information is available from these small studies to evaluate the efficacy of this vaccine against RSV-induced disease. A further problem facing subunit RSV vaccines is the possibility that inoculation of seronegative subjects with immunogenic preparations might result in disease enhancement (sometimes referred to as immunopotentiation), similar to that seen in formalin inactivated RSV vaccines. In some studies, the immune response to immunization with RSV F protein or a synthetic RSV FG fusion protein resulted in a disease enhancement in rodents resembling that induced by a formalin-inactivated RSV vaccine. The association of immunization with disease enhancement using non- replicating antigens suggests caution in their use as vaccines in seronegative humans.

Live attenuated vaccines against disease caused by RSV may be promising for two main reasons. Firstly, infection by a live vaccine virus induces a balanced immune response comprising mucosal and serum antibodies and cytotoxic T-lymphocytes. Secondly, infection of infants with live attenuated vaccine candidates or naturally acquired wild-type virus is not associated with enhanced disease upon subsequent natural reinfection. It will be challenging to produce live attenuated vaccines that are immunogenic for younger infants who possess maternal virus-neutralizing antibodies and yet are attenuated for seronegative infants greater than or equal to 6 months of age. Attenuated live virus vaccines also have the risks of residual virulence and genetic instability.

Injection of plasmid DNA containing sequences encoding a foreign protein has been shown to result in expression of the foreign protein and the induction of antibody and cytotoxic T-lymphocyte responses to the antigen in a number of studies (see, for example, refs. 7, 8, 9). The use of plasmid DNA inoculation to express viral proteins for the purpose of immunization may offer several advantages over the strategies summarized above. Firstly, DNA encoding a viral antigen can be introduced in the presence of antibody to the virus itself, without loss of potency due to neutralization of virus by the antibodies. Secondly, the antigen expressed in vivo should exhibit a native conformation and, therefore, should induce an antibody response similar to that induced by the antigen present in the wild-type virus infection. In contrast, some processes used in purification of proteins can induce conformational changes which may result in the loss of immunogenicity of protective epitopes and possibly immunopotentiation. Thirdly, the expression of proteins from injected plasmid DNAs can be detected in vivo for a considerably longer period of time than that in virus-infected cells, and this has the theoretical advantage of prolonged cytotoxic T-cell induction and enhanced antibody responses. Fourthly, in vivo expression of antigen may provide protection without the need for an extrinsic adjuvant.

The ability to immunize against disease caused by RSV by administration of a DNA molecule encoding an RSV F protein was unknown before the present invention. In particular, the efficacy of immunization against RSV induced disease using a gene encoding a secreted form of the RSV F protein was unknown. Infection with RSV leads to serious disease. It would be useful and desirable to provide isolated genes encoding RSV F protein and vectors for in vivo administration for use in immunogenic preparations, including vaccines, for protection against disease caused by RSV and for the generation of diagnostic reagents and kits. In particular, it would be desirable to provide vaccines that are immunogenic and protective in humans, including seronegative infants, that do not cause disease enhancement (immunopotentiation).

SUMMARY OF INVENTION

The present invention relates to a method of immunizing a host against disease caused by respiratory syncytial virus, to nucleic acid molecules used therein, and to diagnostic procedures utilizing the nucleic acid molecules. In particular, the present invention is directed towards the provision of nucleic acid respiratory syncytial virus vaccines.

In accordance with one aspect of the invention, there is provided a vector, comprising:

a first nucleotide sequence encoding an RSV F protein or a protein capable of inducing antibodies that specifically react with RSV F protein;

a promoter sequence operatively coupled to the first nucleotide sequence for expression of the RSV F protein, and a second nucleotide sequence located adjacent the first nucleotide sequence to enhance the immunoprotective ability of the RSV F protein when expressed in vivo from the vector in a host.

The first nucleotide sequence may be that which encodes a full-length RSV F protein, as seen in FIG. 2 (SEQ ID No: 2). Alternatively, the first nucleotide sequence may be that which encodes an RSV F protein from which the transmembrane region is absent. The latter embodiment may be provided by a nucleotide sequence which encodes a full-length RSV F protein but contains a translational stop codon immediately upstream of the start of the transmembrane coding region, thereby preventing expression of a transmembrane region of the RSV F protein, as seen in FIG. 3 (SEQ. ID No. 4). The lack of expression of the transmembrane region results in a secreted form of the RSV F protein.

The second nucleotide sequence may comprise a pair of splice sites to prevent aberrant mRNA splicing, whereby substantially all transcribed mRNA encodes the RSV protein. Such second nucleotide sequence may be located between the first nucleotide sequence and the promoter sequence. Such second nucleotide sequence may be that of rabbit β-globin intron II, as shown in FIG. 8 (SEQ ID No: 5).

A vector encoding the F protein and provided by this aspect of the invention may specifically be pXL2 or pXL4, as seen in FIGS. 5 or 7.

The promoter sequence may be an immediate early cytomegalovirus (CMV) promoter. Such cytomegalovirus promoter has not previously been employed in vectors containing nucleotide sequences encoding an RSV F protein.

Accordingly, in another aspect of the invention, there is provided a vector, comprising:

a first nucleotide sequence encoding an RSV F protein or a protein capable of generating antibodies that specifically react with RSV F protein, and a cytomegalovirus promoter operatively coupled to the first nucleotide sequence for expression of the RSV F protein.

The first nucleotide sequence may be any of the alternatives described above. The second nucleotide sequence, included to enhance the immunoprotective ability of the RSV F protein when expressed in vivo from the vector in a host, described above also may be present located adjacent a first nucleotide sequence in a vector provided in accordance with this second aspect of the invention.

Certain of the vectors provided herein may be used to immunize a host against RSV infection or disease by in vivo expression of RSV F protein lacking a transmembrane region following administration of the vectors. In accordance with a further aspect of the present invention, therefore, there is provided a method of immunizing a host against disease caused by infection with respiratory syncytial virus, which comprises administering to the host an effective amount of a vector comprising a first nucleotide sequence encoding an RSV F protein, a protein capable of generating antibodies that specifically react with RSV F protein or an RSV F protein lacking a transmembrane region and a promoter sequence operatively coupled to the first nucleotide sequence for expression of the RSV F protein in the host, which may be a human. The promoter may be an immediate early cytomegalovirus promoter.

The nucleotide sequence encoding the truncated RSV F protein lacking the transmembrane region may be that as described above.

A vector containing a second nucleotide sequence located adjacent a first nucleotide sequence encoding an RSV F protein, a protein capable of inducing antibodies that specifically react with RSV F protein or an RSV F protein lacking a transmembrane region and effective to enhance the immunoprotective ability of the RSV F protein expressed by the first nucleotide sequence may be used to immunize a host. Accordingly, in an additional aspect of the present invention, there is provided a method of immunizing a host against disease caused by infection with respiratory syncytial virus (RSV), which comprises administering to the host an effective amount of a vector comprising a first nucleotide sequence encoding an RSV F protein, a protein capable of generating antibodies that specifically react with RSV F protein or an RSV F protein lacking a transmembrane region, a promoter sequence operatively coupled to the first nucleotide sequence for expression of the RSV F protein, and a second nucleotide sequence located adjacent the first sequence to enhance the immunoprotective ability of the RSV-F protein when expressed in vivo from said vector in said host. Specific vectors which may be used in this aspect of the invention are those identified as pXL2 and pXL4 in FIGS. 5 and 7.

The present invention also includes a novel method of using a gene encoding an RSV F protein, a protein capable of generating antibodies that specifically react with RSV F protein or an RSV F protein lacking a transmembrane region to protect a host against disease caused by infection with respiratory syncytial virus, which comprises:

isolating the gene;

operatively linking the gene to at least one control sequence to produce a vector, said control sequence directing expression of the RSV F protein when said vector is introduced into a host to produce an immune response to the RSV F protein, and introducing the vector into the host.

The procedure provided in accordance with this aspect of the invention may further include the step of:

operatively linking the gene to an immunoprotection enhancing sequence to produce an enhanced immunoprotection by the RSV F protein in the host, preferably by introducing the immunoprotection enhancing sequence between the control sequence and the gene.

In addition, the present invention includes a method of producing a vaccine for protection of a host against disease caused by infection with respiratory syncytial virus, which comprises:

isolating a first nucleotide sequence encoding an RSV F protein, a protein capable of generating antibodies that specifically react with RSV F protein or an RSV F protein lacking a transmembrane region;

operatively linking the first nucleotide sequence to at least one control sequence to produce a vector, the control sequence directing expression of the RSV F protein when introduced into a host to produce an immune response to the RSV F protein when expressed in vivo from the vector in a host, and formulating the vector as a vaccine for in vivo administration.

The first nucleotide sequence further may be operatively linked to a second nucleotide sequence to enhance the immunoprotective ability of the RSV F protein when expressed in vivo from the vector in a host. The vector may be selected from pXL1, pXL2 and pXL4. The invention further includes a vaccine for administration to a host, including a human host, produced by this method as well as immunogenic compositions comprising an immunoeffective amount of the vectors described herein.

As noted previously, the vectors provided herein are useful in diagnostic applications. In a further aspect of the invention, therefore, there is provided a method of determining the presence of an RSV F protein in a sample, comprising the steps of:

(a) immunizing a host with a vector comprising a first nucleotide sequence encoding an RSV F protein, a protein capable of generating antibodies that specifically react with RSV F protein or an RSV F protein lacking a transmembrane region and a promoter sequence operatively coupled to the first nucleotide sequence for expression of the RSV F protein in the host to produce antibodies specific for the RSV F protein;

(b) isolating the RSV F protein specific antibodies;

(c) contacting the sample with the isolated antibodies to produce complexes comprising any RSV F protein present in the sample and the RSV F protein- specific antibodies; and (d) determining production of the complexes.

The vector employed to elicit the antibodies may be pXL1, pXL2, pXL3 or pXL4.

The invention also includes a diagnostic kit for detecting the presence of an RSV F protein in a sample, comprising:

(a) a vector comprising a first nucleotide sequence encoding an RSV F protein, a protein capable of generating antibodies that specifically react with RSV F protein, or a RSV F protein lacking a transmembrane region and a promoter sequence operatively coupled to said first nucleotide sequence for expression of said RSV F protein in a host immunized therewith to produce antibodies specific for the RSV F protein;

(b) isolation means to isolate said RSV F protein specific antibodies;

(c) contacting means to contact the isolated RSV F specific antibodies with the sample to produce a complex comprising any RSV F protein present in the sample and RSV F protein specific antibodies; and (d) identifying means to determine production of the complex.

The present invention is further directed to immunization wherein the polynucleotide is an RNA molecule which codes for an RSV F protein, a protein capable of inducing antibodies that specifically react with RSV F protein or an RSV F protein lacking a transmembrane region.

The present invention is further directed to a method for producing RSV F protein specific polyclonal antibodies comprising the use of the immunization method described herein, and further comprising the step of isolating the RSV F protein specific polyclonal antibodies from the immunized animal.

The present invention is also directed to a method for producing monoclonal antibodies specific for an F protein of RSV, comprising the steps of:

(a) constructing a vector comprising a first nucleotide sequence encoding a RSV F protein and a promoter sequence operatively coupled to said first nucleotide sequence for expression of said RSV F protein; and, optionally, a second nucleotide sequence located adjacent said first nucleotide sequence to enhance the immunoprotective ability of said RSV F protein when expressed in vivo from said vector in a host.

(b) administering the vector to at least one mouse to produce at least one immunized mouse;

(c) removing B-lymphocytes from the at least one immunized mouse;

(d) fusing the B-lymphocytes from the at least one immunized mouse with myeloma cells, thereby producing hybridomas;

(e) cloning the hybridomas;

(f) selecting clones which produce anti-F protein antibody;

(g) culturing the anti-F protein antibody-producing clones; and (h) isolating anti-F protein monoclonal antibodies.

In this application, the term "RSV F protein" is used to define a full-length RSV F protein, such proteins having variations in their amino acid sequences including those naturally occurring in various strains of RSV, a secreted form of RSV F protein lacking a transmembrane region, as well as functional analogs of the RSV F protein. In this application, a first protein is a "functional analog" of a second protein if the first protein is immunologically related to and/or has the same function as the second protein. The functional analog may be, for example, a fragment of the protein or a substitution, addition or deletion mutant thereof.

BRIEF DESCRIPTION OF THE FIGURES

The present invention will be further understood from the following General Description and Examples with reference to the Figures in which:

FIG. 1 illustrates a restriction map of the gene encoding the F protein of Respiratory Syncytial Virus;

FIG. 2 illustrates the nucleotide sequence of the gene encoding the membrane attached form of the F protein of Respiratory Syncytial Virus (SEQ ID No: 1) as well as the amino acid sequence of the RSV F protein encoded thereby (SEQ ID No: 2);

FIG. 3 illustrates the nucleotide sequence of the gene encoding the secreted form of the RSV F protein lacking the transmembrane region (SEQ ID No: 3) as well as the amino acid sequence of the truncated RSV F protein lacking the transmembrane region encoded thereby (SEQ ID No: 4);

FIG. 8 shows the nucleotide sequence for the rabbit β-globin Intron II sequence (SEQ ID No. 5).

GENERAL DESCRIPTION OF INVENTION

As described above, the present invention relates generally to polynucleotide, including DNA, immunization to obtain protection against infection by respiratory syncytial virus (RSV) and to diagnostic procedures using particular vectors. In the present invention, several recombinant vectors were constructed to contain a nucleotide sequence encoding an RSV F protein.

The nucleotide sequence of the full length RSV F gene is shown in FIG. 2 (SEQ ID No: 1). Certain constructs provided herein include the nucleotide sequence encoding the full-length RSV F (SEQ ID No: 2) protein while others include an RSV F gene modified by insertion of termination codons immediately upstream of the transmembrane coding region (see FIG. 3, SEQ ID No: 3), to prevent expression of the transmembrane portion of the protein and to produce a secreted or truncated RSV F protein lacking a transmembrane region (SEQ ID No. 4).

The nucleotide sequence encoding the RSV F protein is operatively coupled to a promoter sequence for expression of the encoded RSV F protein. The promoter sequence may be the immediately early cytomegalovirus (CMV) promoter. This promoter is described in ref. 13. Any other convenient promoter may be used, including constitutive promoters, such as, Rous Sarcoma Virus LTRs, and inducible promoters, such as metallothionine promoter, and tissue specific promoters.

Figure 4A:
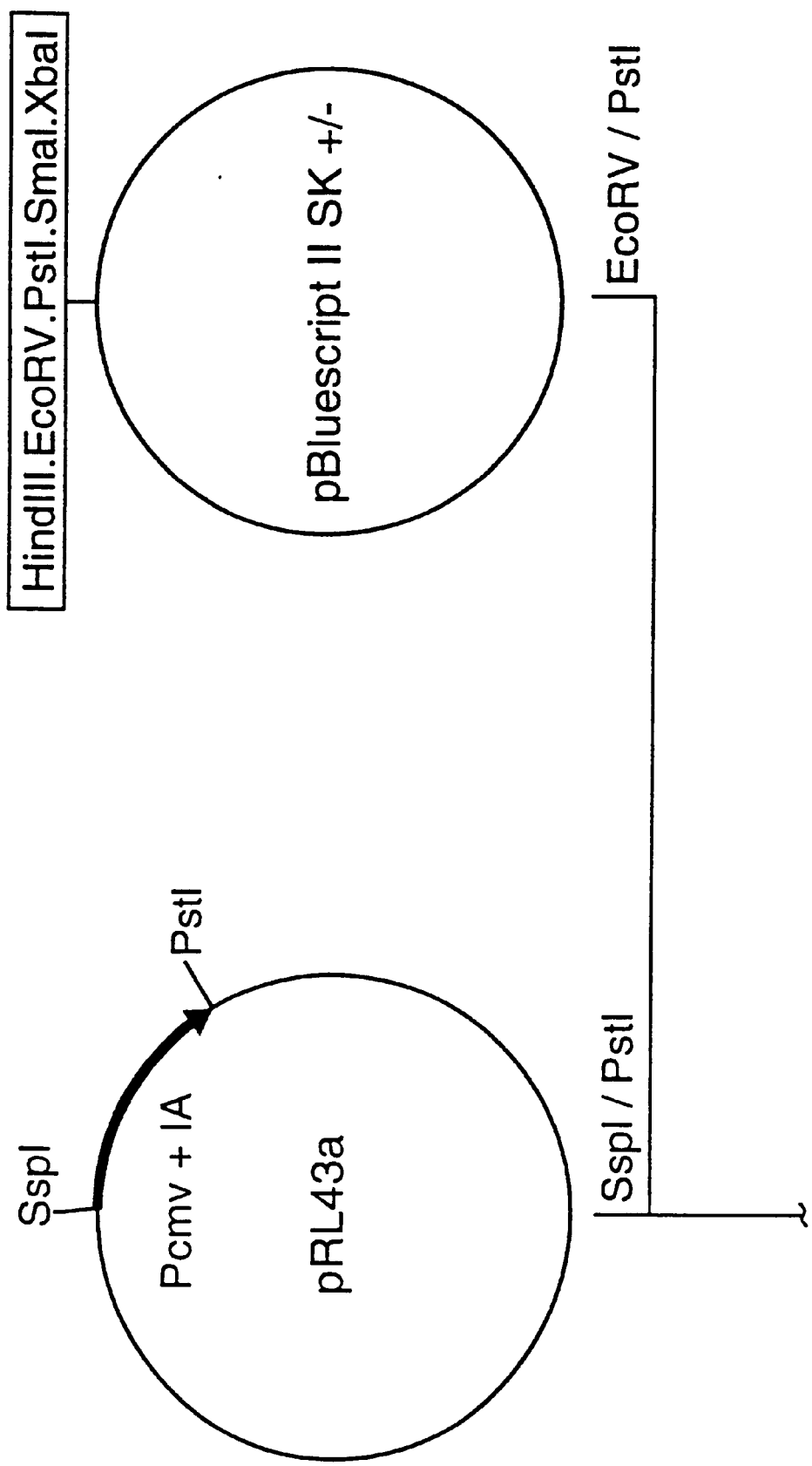
FIGS. 4A to 4D show the construction of plasmid pXL1 containing the gene encoding a secreted form of the RSV F protein lacking the transmembrane region.
Figure 4B:
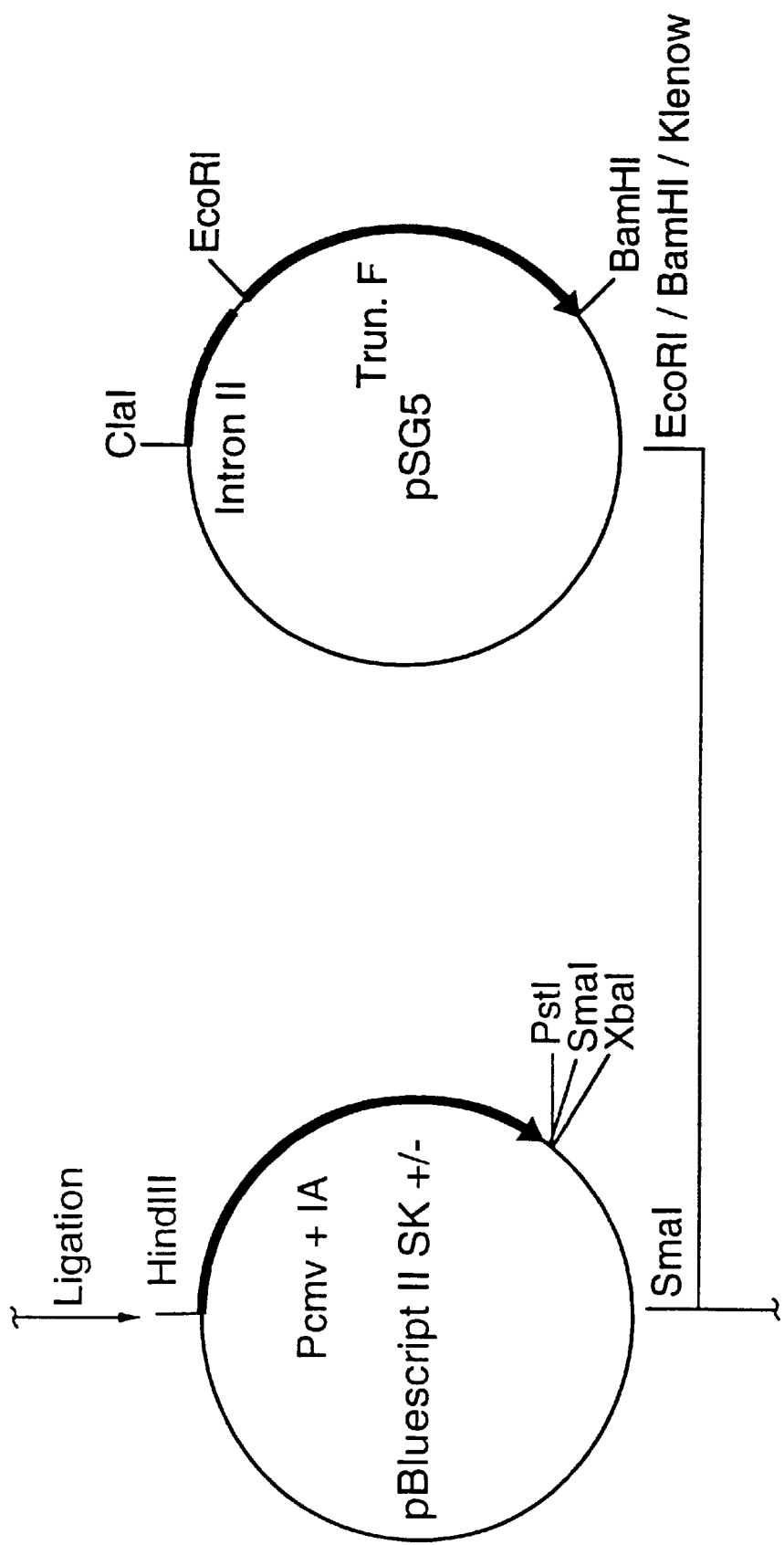
Figure 4C:
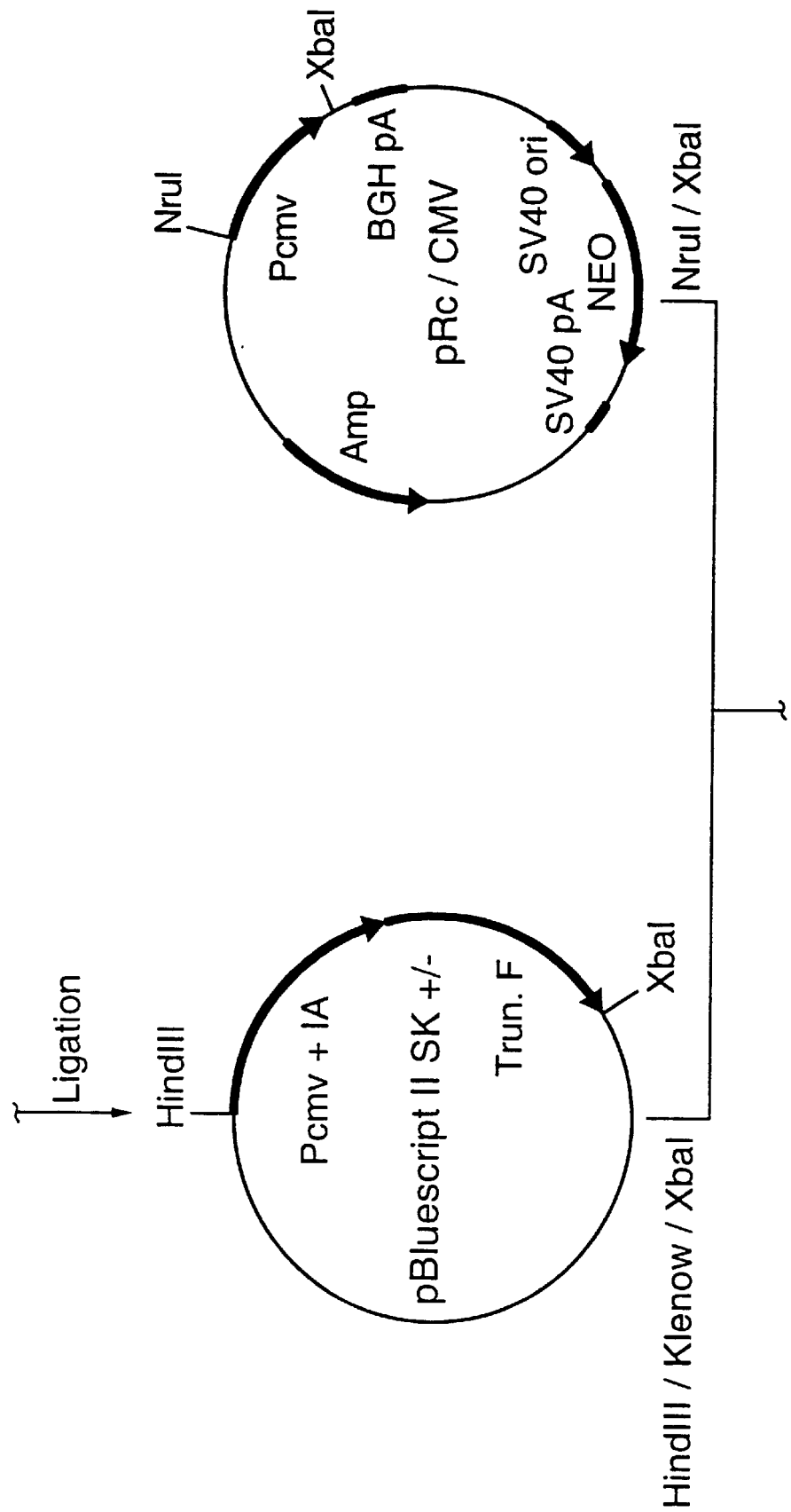
Figure 4D:
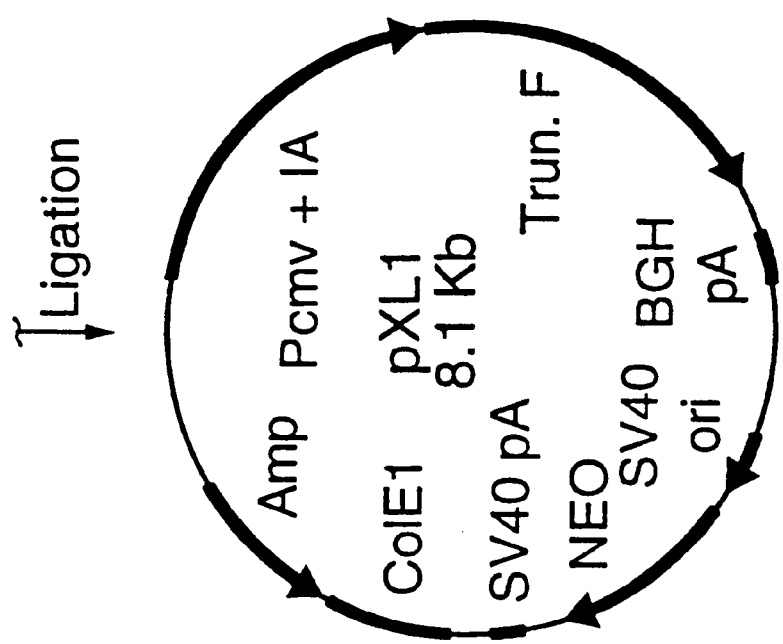

The vectors provided herein, when administered to an animal, effect in vivo RSV F protein expression, as demonstrated by an antibody response in the animal to which it is administered. Such antibodies may be used herein in the detection of RSV protein in a sample, as described in more detail below. When the encoded RSV F protein is in the form of an RSV F protein from which the transmembrane region is absent, such as plasmid pXL1 (FIG. 4), the administration of the vector conferred protection in mice and cotton rats to challenge by live RSV virus neutralizing antibody and cell mediated immune responses and an absence of immunopotentiation in immunized animals, as seen from the Examples below.

The recombinant vector also may include a second nucleotide sequence located adjacent the RSV F protein encoding nucleotide sequence to enhance the immunoprotective ability of the RSV F protein when expressed in vivo in a host. Such enhancement may be provided by increased in vivo expression, for example, by increased mRNA stability, enhanced transcription and/or translation. This additional sequence preferably is located between the promoter sequence and the RSV F protein-encoding sequence.

Figure 7A:
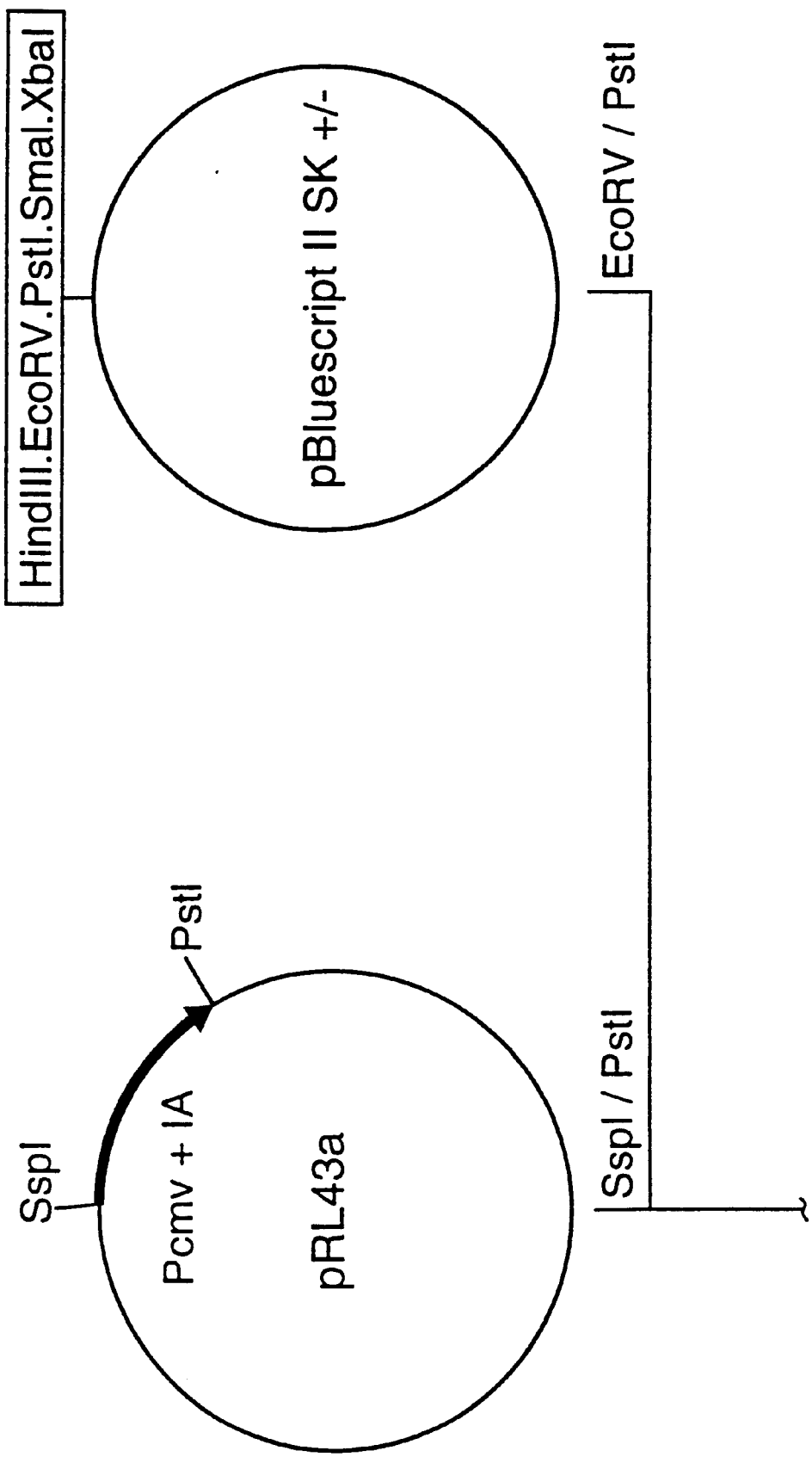
FIGS. 7A to 7D show the construction of plasmid pXL4 containing a gene encoding a membrane attached form of the RSV F protein and containing the rabbit β-globin Intron II sequence.
Figure 7B:
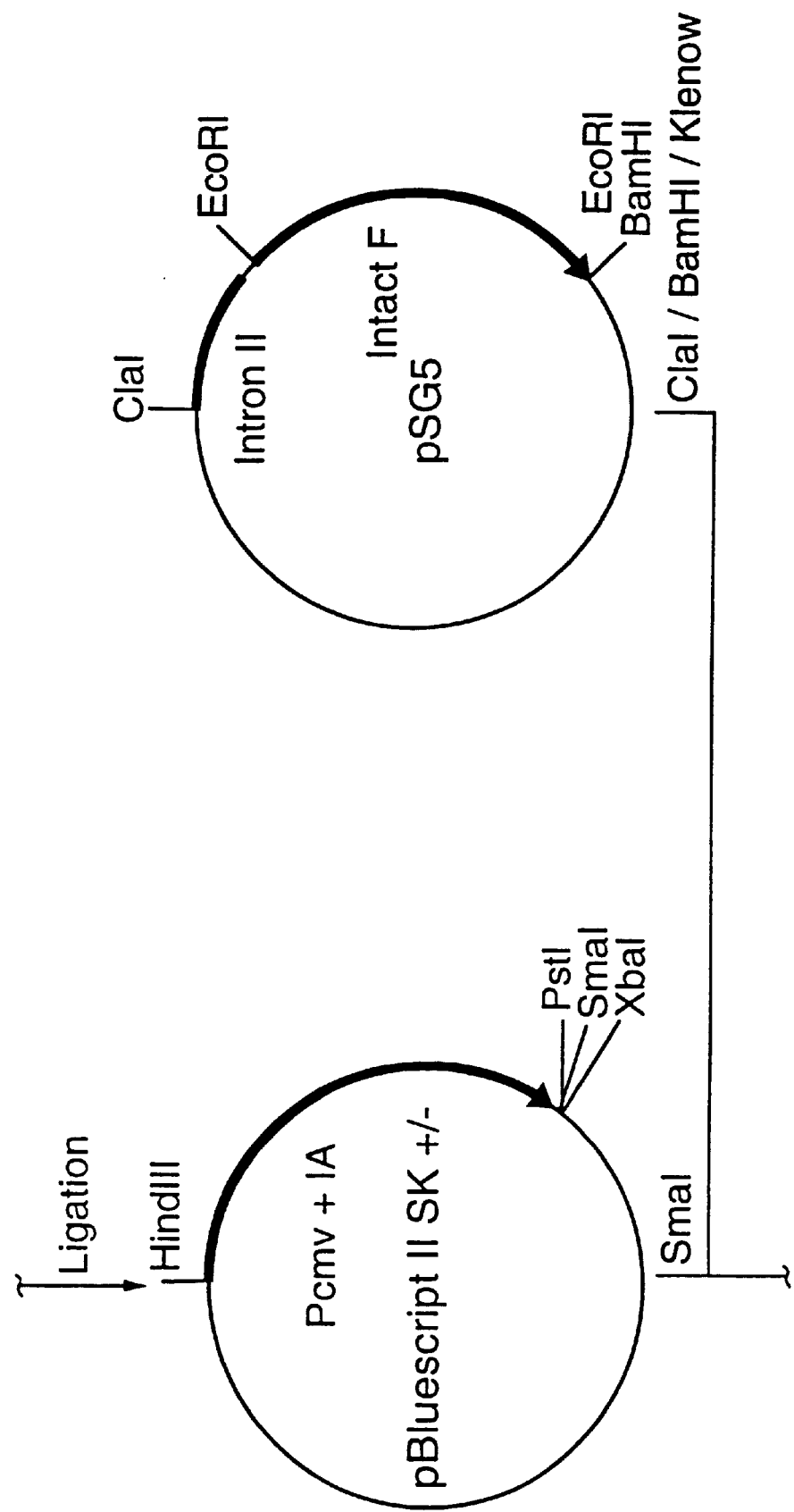
Figure 7C:
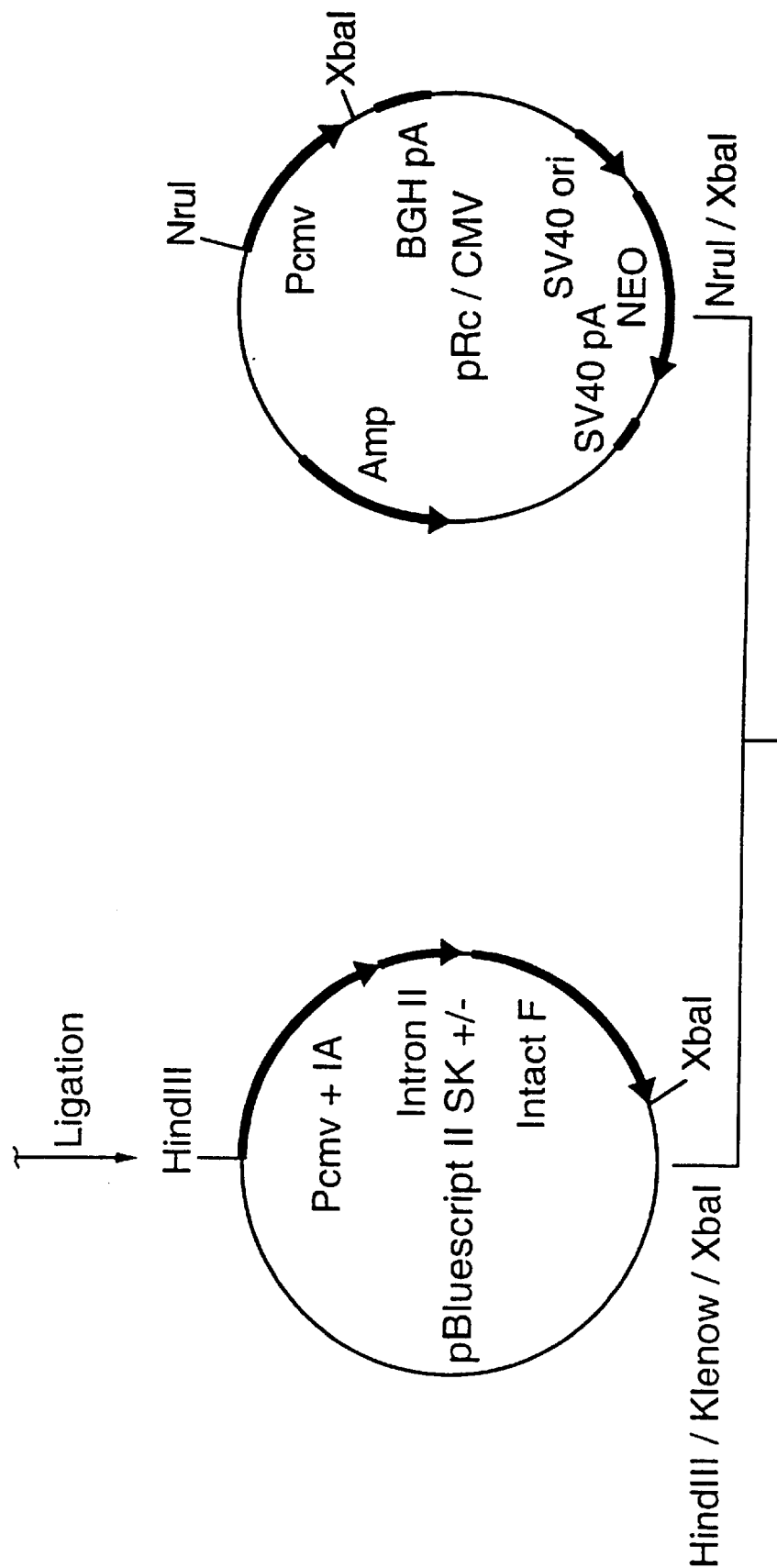
Figure 7D:
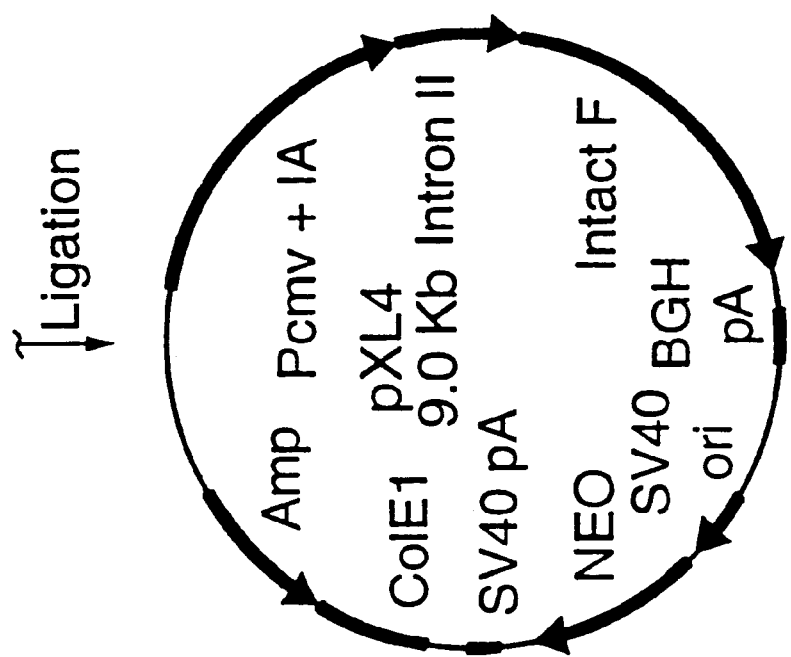

This enhancement sequence may comprise a pair of splice sites to prevent aberrant mRNA splicing during transcription and translation so that substantially all transcribed mRNA encodes an RSV F protein. Specifically, rabbit β-globin Intron II sequence shown in FIG. 7 (SEQ ID No: 5) may provide such splice sites, as also described in ref. 15.

Figure 5A:
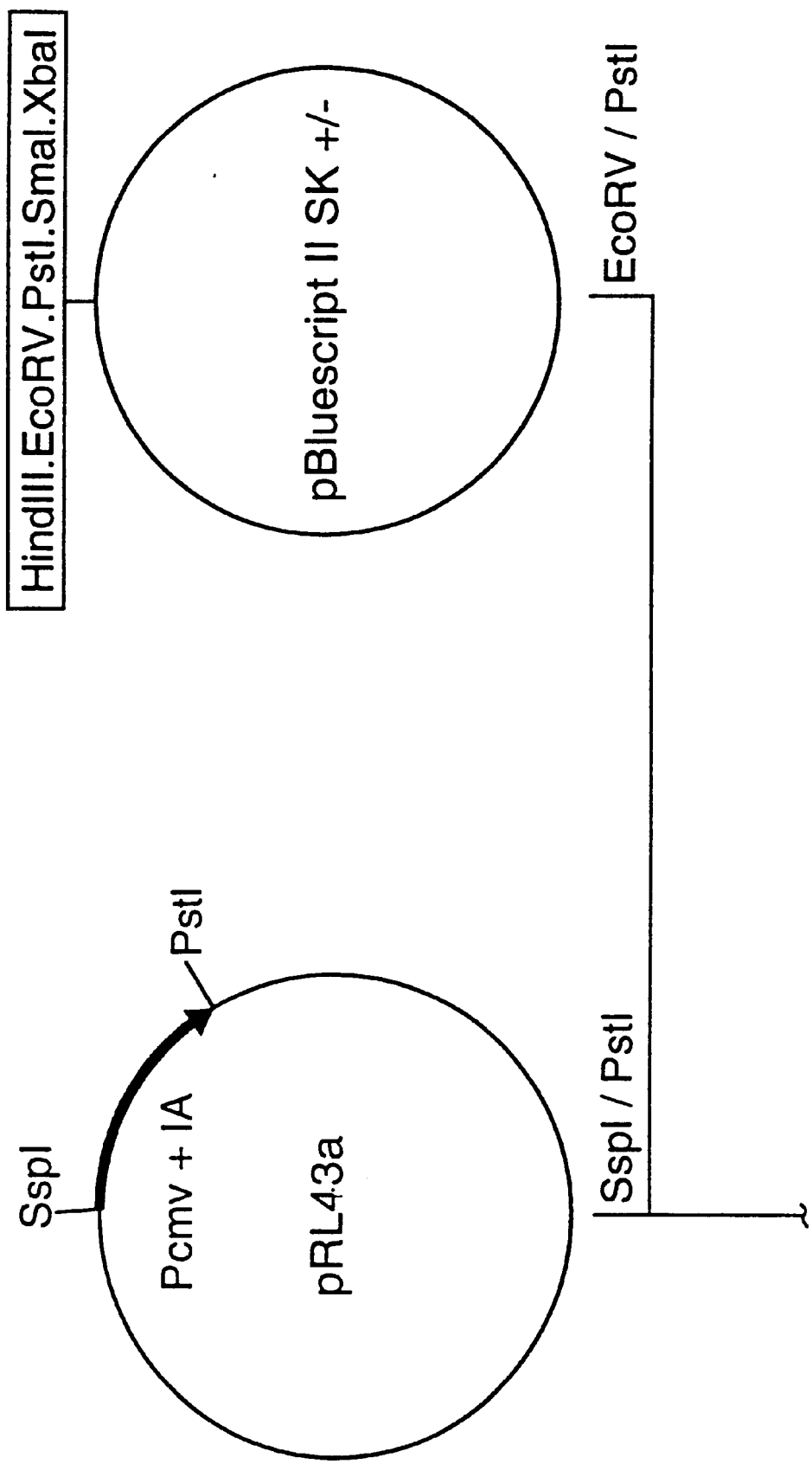
FIGS. 5A to 5D show the construction of plasmid pXL2 containing a gene encoding a secreted form of the RSV F protein lacking the transmembrane region and containing the rabbit β-globin Intron II sequence.
Figure 5B:
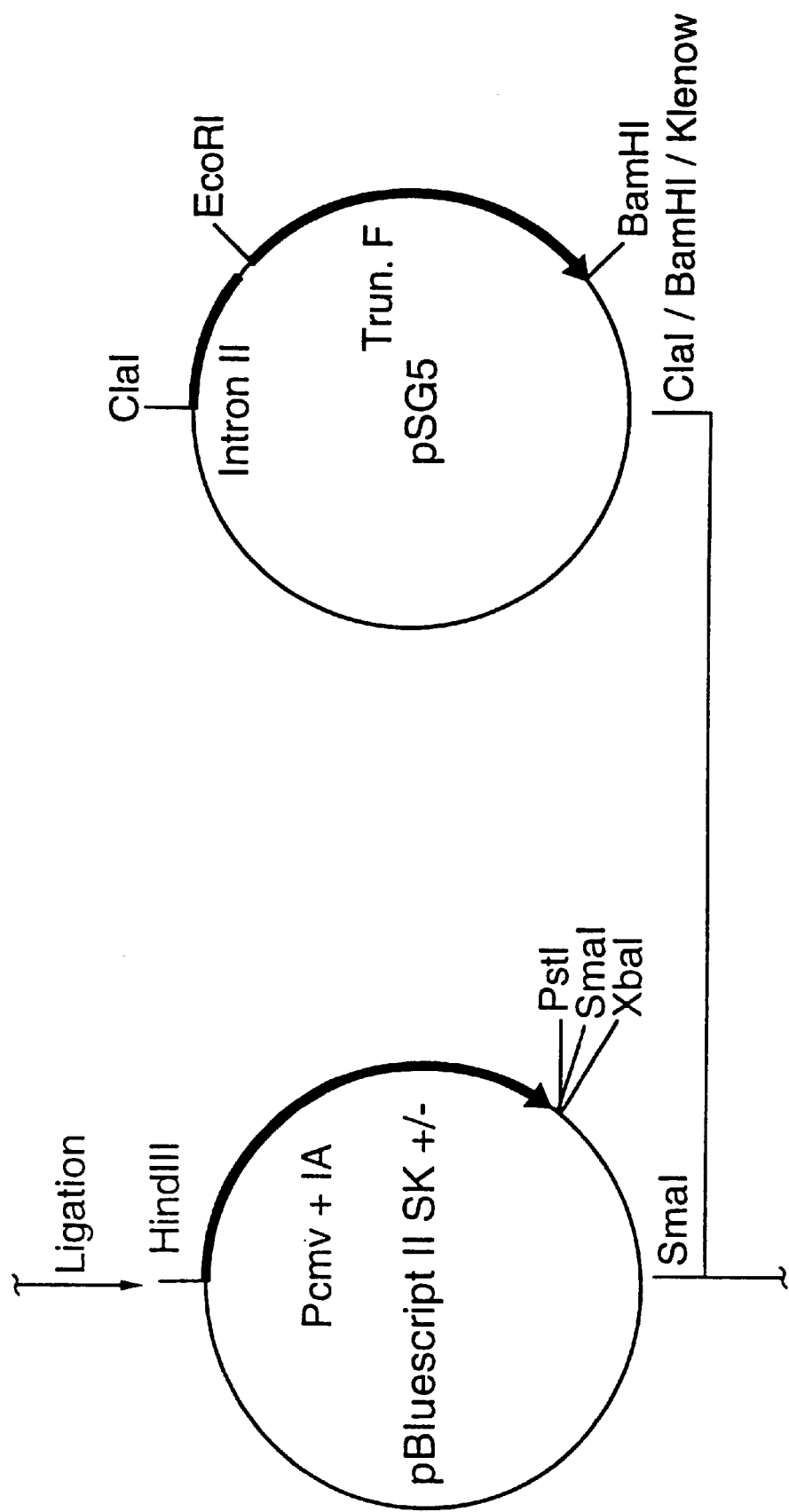
Figure 5C:
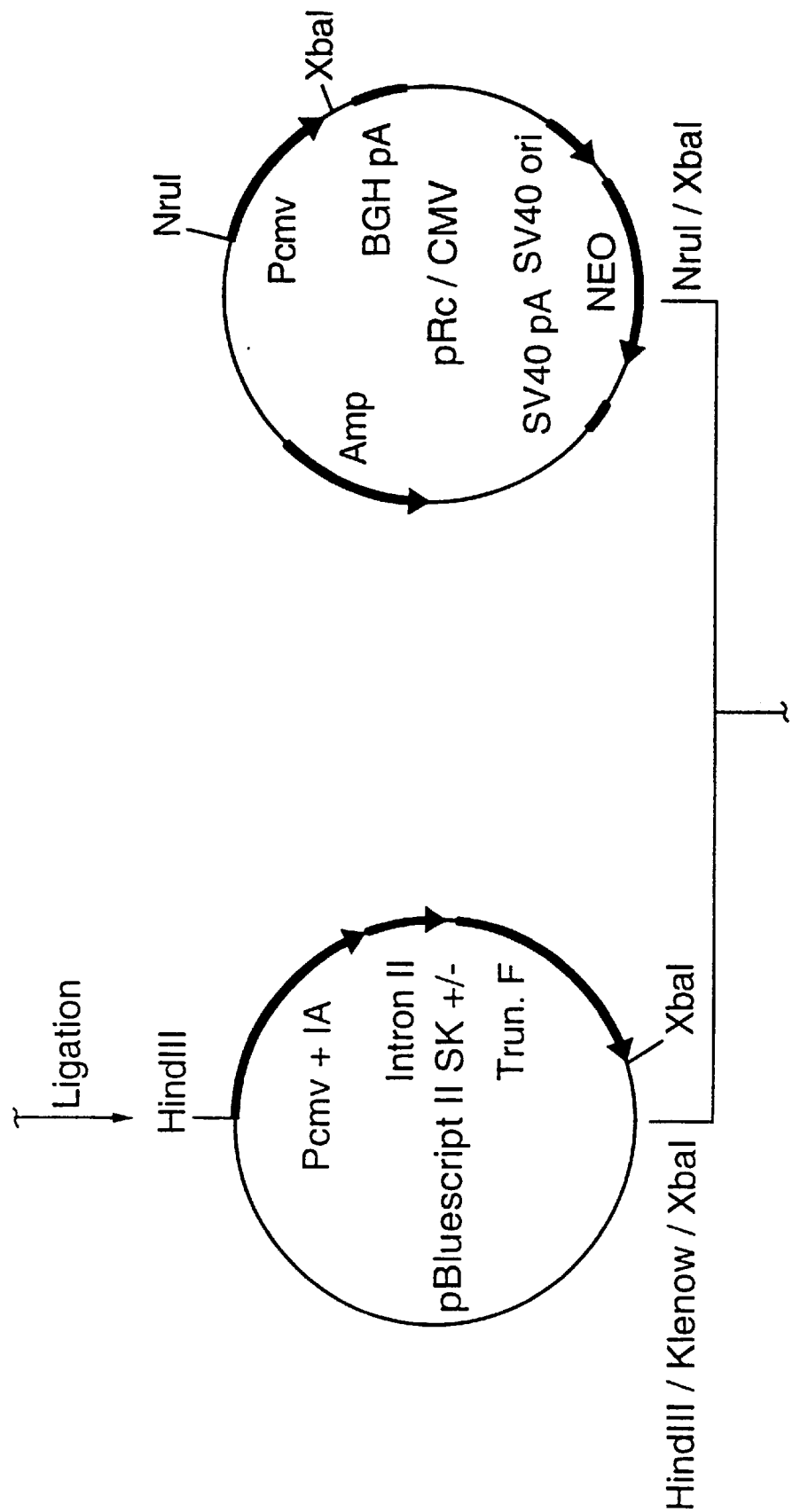
Figure 5D:
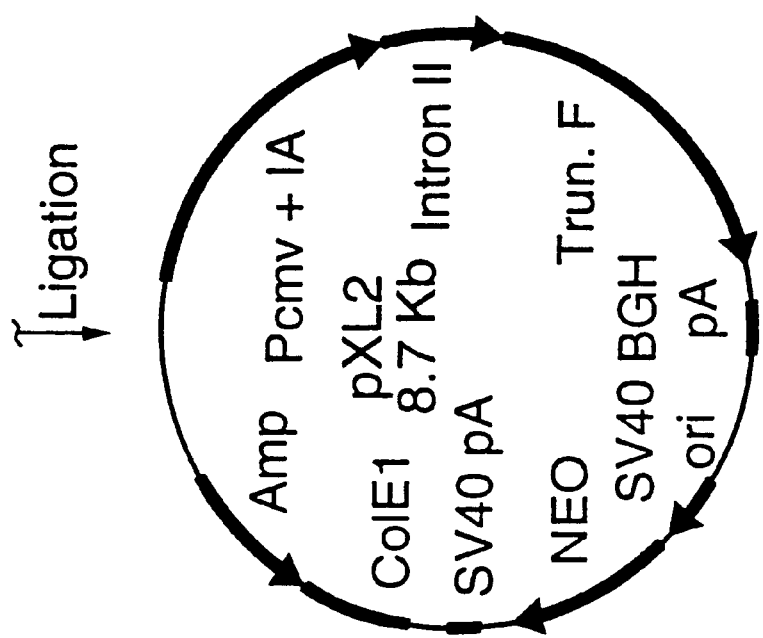

The constructs containing the Intron II sequence, CMV promoter and nucleotide sequence coding for the truncated RSV F protein lacking a transmembrane region, i.e. plasmid pXL2 (FIG. 5), induced complete protection in mice against challenge with live RSV, as seen in the Examples below. In addition, the constructs containing the Intron II sequence, CMV promoter and nucleotide sequence coding for the full-length RSV F protein, i.e. plasmid pXL4 (FIG. 7), also conferred protection in mice to challenge with live RSV, as seen from the Examples below.

The vector provided herein may also comprise a third nucleotide sequence encoding a further antigen from RSV, an antigen from at least one other pathogen or at least one immunomodulating agent, such as cytokine. Such vector may contain said third nucleotide sequence in a chimeric or a bicistronic structure. Alternatively, vectors containing the third nucleotide sequence may be separately constructed and coadministered to a host, with the nucleic acid molecule provided herein.

The vector may further comprise a nucleotide sequence encoding a heterologous signal peptide, such as human tissue plasminogen activator (TPA), in place of the endogenous signal peptide.

It is clearly apparent to one skilled in the art, that the various embodiments of the present invention have many applications in the fields of vaccination, diagnosis and treatment of RSV infections. A further non-limiting discussion of such uses is further presented below.

1. Vaccine Preparation and Use

Immunogenic compositions, suitable to be used as vaccines, may be prepared from the RSV F genes and vectors as disclosed herein. The vaccine elicits an immune response in a subject which includes the production of anti-F antibodies. Immunogenic compositions, including vaccines, containing the nucleic acid may be prepared as injectables, in physiologically-acceptable liquid solutions or emulsions for polynucleotide administration. The nucleic acid may be associated with liposomes, such as lecithin liposomes or other liposomes known in the art, as a nucleic acid liposome (for example, as described in WO 9324640, ref. 17) or the nucleic acid may be associated with an adjuvant, as described in more detail below. Liposomes comprising cationic lipids interact spontaneously and rapidly with polyanions such as DNA and RNA, resulting in liposome/nucleic acid complexes that capture up to 100% of the polynucleotide. In addition, the polycationic complexes fuse with cell membranes, resulting in an intracellular delivery of polynucleotide that bypasses the degradative enzymes of the lysosomal compartment. Published PCT application WO 94/27435 describes compositions for genetic immunization comprising cationic lipids and polynucleotides. Agents which assist in the cellular uptake of nucleic acid, such as calcium ions, viral proteins and other transfection facilitating agents, may advantageously be used.

Polynucleotide immunogenic preparations may also be formulated as microcapsules, including biodegradable time-release particles. Thus, U.S. Pat. No. 5,151,264 describes a particulate carrier of a phospholipid/glycolipid/polysaccharide nature that has been termed Bio Vecteurs Supra Moléculaires (BVSM). The particulate carriers are intended to transport a variety of molecules having biological activity in one of the layers thereof.

U.S. Pat. No. 5,075,109 describes encapsulation of the antigens trinitrophenylated keyhole limpet hemocyanin and staphylococcal enterotoxin B in 50:50 poly (DL-lactideco-glycolide). Other polymers for encapsulation are suggested, such as poly(glycolide), poly(DL-lactide-co-glycolide), copolyoxalates, polycaprolactone, poly(lactide-co-caprolactone), poly(esteramides), polyorthoesters and poly (8-hydroxybutyric acid), and polyanhydrides.

Published PCT application WO 91/06282 describes a delivery vehicle comprising a plurality of bioadhesive microspheres and antigens. The microspheres being of starch, gelatin, dextran, collagen or albumin. This delivery vehicle is particularly intended for the uptake of vaccine across the nasal mucosa. The delivery vehicle may additionally contain an absorption enhancer.

The RSV F genes and vectors may be mixed with pharmaceutically acceptable excipients which are compatible therewith. Such excipients may include, water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneously, intravenously, intradermally or intramuscularly, possibly following pretreatment of the injection site with a local anesthetic. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Oral formulations may include normally employed incipients, such as, for example, pharmaceutical grades of saccharine, cellulose and magnesium carbonate.

The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune system to synthesize the RSV F protein and antibodies thereto, and if needed, to produce a cell-mediated immune response. Precise amounts of active ingredient required to be administered depend on the judgment of the practitioner. However, suitable dosage ranges are readily determinable by one skilled in the art and may be of the order of about 1 $\mu$g to about 1 mg of the RSV F genes and vectors. Suitable regimes for initial administration and booster doses are also variable, but may include an initial administration followed by subsequent administrations. The dosage may also depend on the route of administration-and will vary according to the size of the host. A vaccine which protects against only one pathogen is a monovalent vaccine. Vaccines, which contain antigenic material of several pathogens are combined vaccines and also belong to the present invention. Such combined vaccines contain, for example, material from various pathogens or from various strains of the same pathogen, or from combinations of various pathogens.

Immunogenicity can be significantly improved if the vectors are co-administered with adjuvants, commonly used as 0.05 to 0.1 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Thus, adjuvants have been identified that enhance the immune response to antigens. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines.

A wide range of extrinsic adjuvants and other immuno-modulating material can provoke potent immune responses to antigens. These include saponins complexed to membrane protein antigens to produce immune stimulating complexes (ISCOMS), pluronic polymers with mineral oil, killed mycobacteria in mineral oil, Freund's complete adjuvant, bacterial products, such as muramyl dipeptide (MDP) and lipopolysaccharide (LPS), as well as monophoryl lipid A, QS 21 and polyphosphazene.

In particular embodiments of the present invention, the vector comprising a first nucleotide sequence encoding an F protein of RSV may be delivered in conjunction with a targeting molecule to target the vector to selected cells including cells of the immune system.

The polynucleotide may be delivered to the host by a variety of procedures, for example, Tang et al. (ref. 10) disclosed that introduction of gold microprojectiles coated with DNA encoding bovine growth hormone (BGH) into the skin of mice resulted in production of anti-BGH antibodies in the mice, while Furth et al. (ref. 11) showed that a jet injector could be used to transfect skin, muscle, fat and mammary tissues of living animals.

2. Immunoassays

The RSV F genes and vectors of the present invention are useful as immunogens for the generation of anti-F antibodies for use in immunoassays, including enzyme-linked immunosorbent assays (ELISA), RIAs and other non-enzyme linked antibody binding assays or procedures known in the art. In ELISA assays, the vector first is administered to a host to generate antibodies specific to the RSV F protein. These RSV F-specific antibodies are immobilized onto a selected surface, for example, a surface capable of binding the antibodies, such as the wells of a polystyrene microtiter plate. After washing to remove incompletely adsorbed antibodies, a nonspecific protein such as a solution of bovine serum albumin (BSA) that is known to be antigenically neutral with regard to the test sample may be bound to the selected surface. This allows for blocking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody)

formation. This procedure may include diluting the sample with diluents, such as solutions of BSA, bovine gamma globulin (BGG) and/or phosphate buffered saline (PBS)/ TWEEN (a non-ionic surfactant). The sample is then allowed to incubate for from about 2 to 4 hours, at temperatures such as of the order of about 20° to 37° C. Following incubation, the sample-contacted surface is washed to remove non-immunocomplexed material. The washing procedure may include washing with a solution, such as PBS/ Tween or a borate buffer. Following formation of specific immunocomplexes between the test sample and the bound RSV F specific antibodies, and subsequent washing, the occurrence, and even amount, of immunocomplex formation may be determined.

BIOLOGICAL MATERIALS

Certain plasmids that contain the gene encoding RSV F protein and referred to herein have been deposited with the America Type Culture Collection (ATCC) located at 10801 University Boulevard, Manassas, Va. 20110-2209, U.S.A., pursuant to the Budapest Treaty and prior to the filing of this application.

Samples of the deposited plasmids will become available to the public upon grant of a patent based upon this United States patent application and all restrictions on access to the deposits will be removed at that time. The invention described and claimed herein is not to be limited in scope by plasmids deposited, since the deposited embodiment is intended only as an illustration of the invention. Any equivalent or similar plasmids that encode similar or equivalent antigens as described in this application are within the scope of the invention.

| Plasmid | ATCC Designation | Date Deposited |
| --- | --- | --- |
| pXL1 | 97167 | May 30, 1995 |
| pXL2 | 97168 | May 30, 1995 |
| pXL3 | 97169 | May 30, 1995 |
| pXL4 | 97170 | May 30, 1995. |

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, and immunology used but not explicitly described in this disclosure and these Examples are amply reported in the scientific literature and are well within the ability of those skilled in the art.

EXAMPLE 1

This Example describes the construction of vectors containing the RSV F gene.

FIG. 1 shows a restriction map of the gene encoding the F protein of Respiratory Syncytial Virus and FIG. 2 shows the nucleotide sequence of the gene encoding the full-length RSV F protein (SEQ ID No: 1) and the deduced amino acid sequence (SEQ ID No: 2). FIG. 3 shows the gene encoding the secreted RSV F protein (SEQ ID No: 3) and the deduced amino acid sequence (SEQ ID No: 4).

Figure 6A:
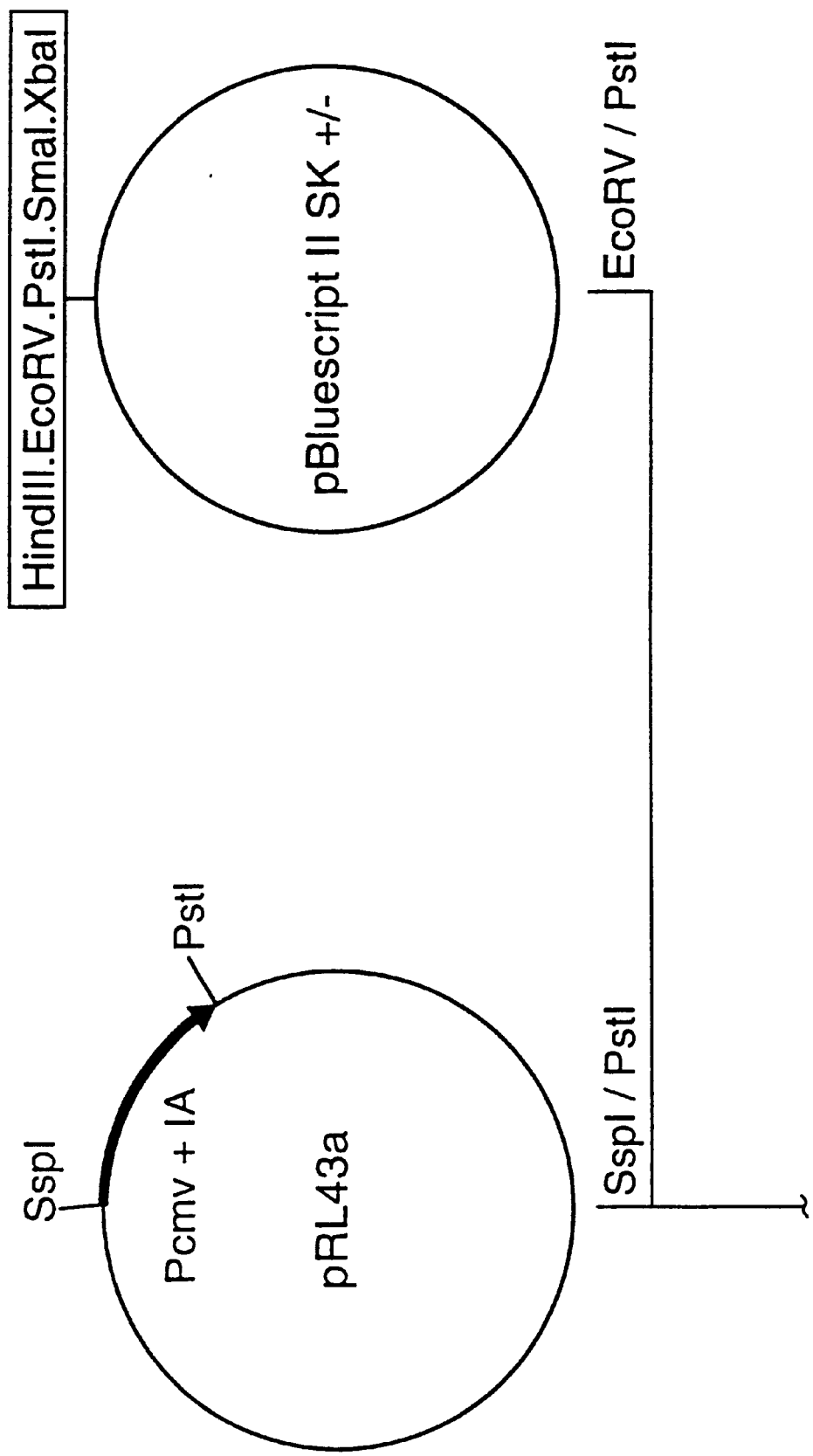
FIGS. 6A to 6D show the construction of plasmid pXL3 containing the gene encoding a full length membrane attached form of the RSV F protein.
Figure 6B:
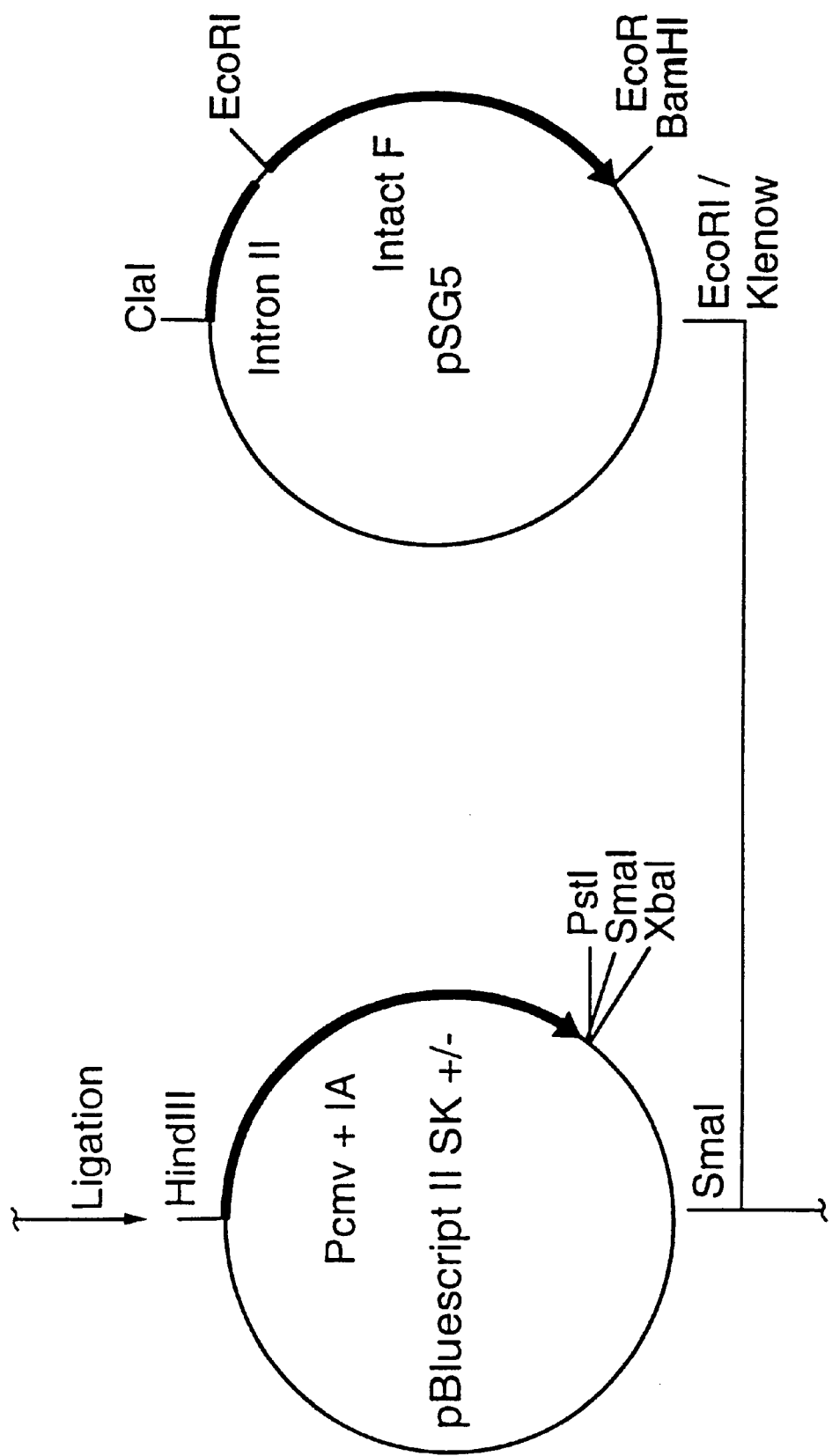
Figure 6C:
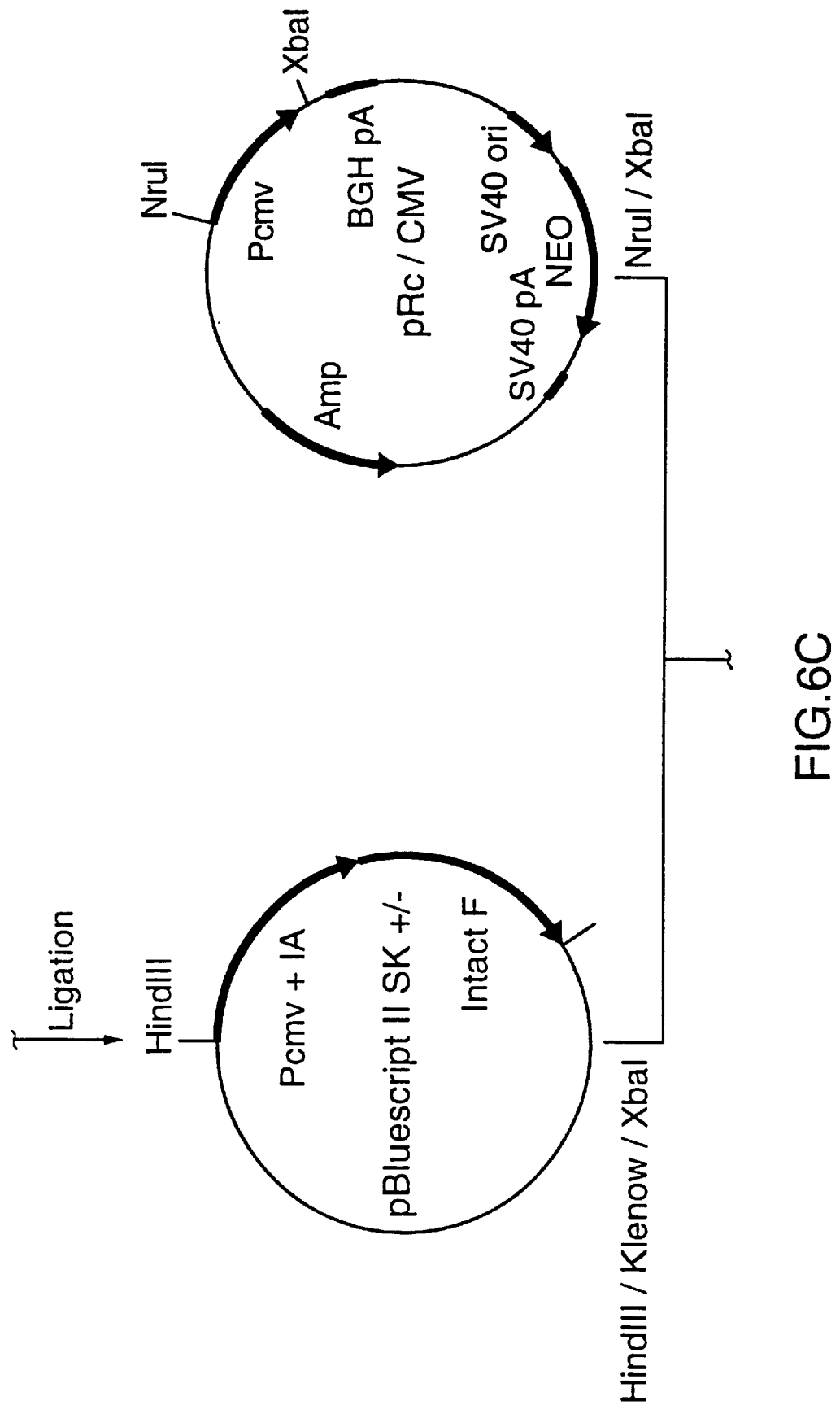
Figure 6D:
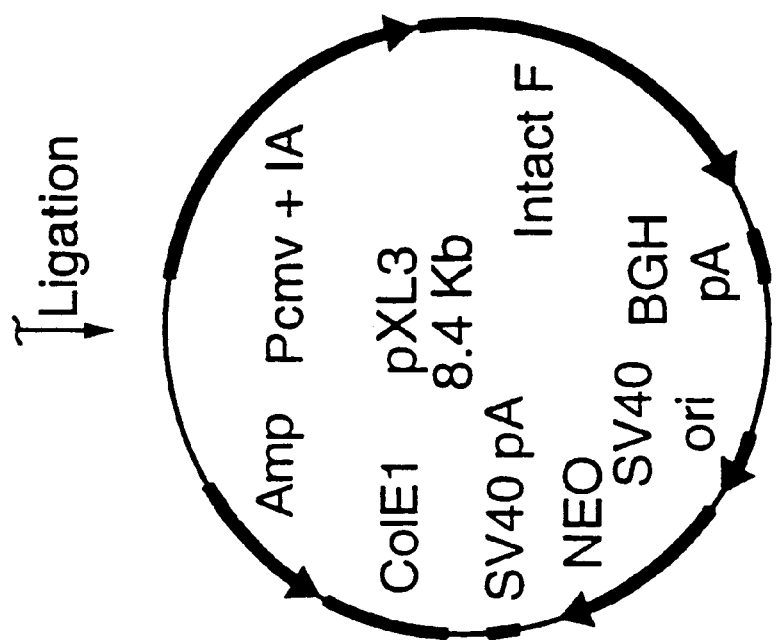

A set of four plasmid DNA constructs were made (as shown schematically in FIGS. 4 to 7) in which cDNA encoding the RSV-F was subcloned downstream of the immediate-early promoter, enhancer and intron A sequences of human cytomegalovirus (CMV) and upstream of the bovine growth hormone (BGH) poly-A site. The 1.6 Kb Sspl-PstI fragment containing the promoter, enhancer and intron A sequences of CMV Towne strain were initially derived from plasmid pRL43a obtained from Dr. G. S. Hayward of Johns Hopkins University (ref. 20) and subcloned between EcoRV and PstI sites of pBluescript 11 SK +/− (Stratagene). For the construction of plasmids expressing the secretory form of the F protein (pXL1 and pXL2 in FIGS. 4 and 5), the 1.6 Kb EcoRI-BamHI fragment containing the truncated form of the F cDNA originally cloned from a clinical isolate belonging to subgroup A was excised from pRSVF (ref. 18 and WO 93/14207) and subcloned between EcoRI and BamHI sites of pSG5 (Strategene, ref. 14). Either the 1.6 kb EcoRI-BamHI fragment or the 2.2 kb ClaI-BamHI fragment was then excised from the pSG5 construct, filled-in with Klenow and subcloned at the SmaI site of the pBluescript II SK +/− construct containing the promoter and intron A sequences. The 0.6 kb ClaI-EcoRI fragment derived from pSG5 contained the intron II sequences from rabbit β-globin. Subsequently, the plasmids were digested with HindIII, filled-in with Klenow, and digested with XbaI to yield either a 3.2 or a 3.8 Kb fragment. These fragments were used to replace the 0.8 kb NruI-XbaI fragment containing the CMV promoter in pRc/CMV (Invitrogen), resulting in the final pXL1 and pXL2 constructs, respectively.

For the construction of plasmids expressing the full-length F protein (pXL3 and pXL4—FIGS. 6 and 7), the full length RSV F cDNA was excised as a 1.9 kb EcoRI fragment from a recombinant pBluescript M13-SK (Stratagene) containing the insert (ref. 18 and WO 93/14207) and subcloned at the EcoRI site of pSG5 (Stratagene). Either the 1.9 Kb EcoRI fragment or the 2.5 Kb ClaI-BamHI fragment was then excised from the pSG5 construct, filled-in with Klenow and subcloned at the SmaI site of the pBluescript II SK +/− construct containing the promoter and intron A sequences. The rest of the construction for pXL3 and pXL4 was identical to that for pXL1 and pXL2, as described above. Therefore, except for the CMV promoter and intron A sequences, the rest of the vector components in pXL1–4 were derived from plasmid pRc/CMV. Plasmids pXL1 and pXL2 were made to express a truncated/secretory form of the F protein which carried stop codons resulting in a C-terminal deletion of 48 amino acids including the transmembrane (TM) and the C-terminal cytosolic tail as compared to the intact molecule. In contrast, pXL3 and pXL4 were made to express the intact membrane-attached form of the RSV F molecule containing the TM and the cytosolic C-terminal tail. The rationale for the presence of the intron II sequences in pXL2 and pXL4 was that this intron was reported to mediate the correct splicing of RNAs. Since mRNA for the RSV-F has been suspected to have a tendency towards aberrant splicing, the presence of the intron II sequences might help to overcome this. All four plasmid constructs were confirmed by DNA sequencing analysis.

Plasmid DNA was purified using plasmid mega kits from Qiagen (Chatsworth, Calif., USA) according to the manufacturer's instructions.

EXAMPLE 2

This Example describes the immunization of mice. Mice are susceptible to infection by RSV as described in ref. 16.

For intramuscular (i.m) immunization, the anterior tibialis anterior muscles of groups of 9 BALB/c mice (male, 6–8 week old) (Jackson Lab., Bar Harbor, Me., USA) were bilaterally injected with 2×50 μg (1 μg/μL in PBS) of pXL1–4, respectively. Five days prior to DNA injection, the muscles were treated with 2×50 μL (10 μM in PBS) of cardiotoxin (Latoxan, France). Pretreatment of the muscles with cardiotoxin has been reported to increase DNA uptake and to enhance the subsequent immune responses by the intramuscular route (ref. 24). These animals were similarly boosted a month later. Mice in the control group were immunized with a placebo plasmid containing identical vector backbone sequences without the RSV F gene according to the same schedule. For intradermal (i.d.) immunization, 100 μg of pXL2 (2 μg/μL in PBS) were injected into the skin 1–2 cm distal from the tall base. The animals were similarly boosted a month later.

Seventy-five days after the second immunization, mice were challenged intranasally with $10^{5.4}$ plaque forming units (pfu) of mouse-adapted RSV, A2 subtype (obtained from Dr. P. Wyde, Baylor College of Medicine, Houston, Tex., USA). Lungs were aseptically removed 4 days later, weighed and homogenized in 2 mL of complete culture medium. The number of pfu in lung homogenates was determined in duplicates as previously described (ref. 19) using vaccine quality Vero cells. These data were subjected to statistic analysis using SigmaStat (Jandel Scientific Software, Guelph, Ont. Canada).

Sera obtained from immunized mice were analyzed for anti-RSV F antibody titres (IgG, IgG1 and IgG2a, respectively) by enzyme-linked immunosorbent assay (ELISA) and for RSV-specific plaque-reduction titres. ELISA were performed using 96-well plates coated with immunoaffinity purified RSV F protein (50 ng/mL) and 2-fold serial dilutions of immune sera. A goat anti-mouse IgG antibody conjugated to alkaline phosphatase (Jackson ImmunoRes., Mississauga, Ont., Canada) was used as secondary antibody. For the measurement of IgG1 and IgG2a antibody titres, the secondary antibodies used were monospecific sheep anti-mouse IgG1 (Serotec, Toronto, Ont., Canada) and rat anti-mouse IgG2a (Zymed, San Francisco, Calif., USA) antibodies conjugated to alkaline phosphatase, respectively. Plaque reduction titres were determined according to Prince et al (ref. 19) using vaccine quality Vero cells. Four-fold serial dilutions of immune sera were incubated with 50 pfu of RSV, Long strain (ATCC) in culture medium at 37° C. for 1 hr in the presence of 5% $CO_2$. Vero cells were then-infected with the mixture. Plaques were fixed with 80% methanol and developed 5 days later using a mouse anti-RSV-F monoclonal IgG1 antibody and donkey antimouse IgG antibody conjugated to peroxidase (Jackson ImmunoRes., Mississauga, Ont. Canada). The RSV-specific plaque reduction titre was defined as the dilution of serum sample yielding 60% reduction in the number of plaques. Both ELISA and plaque reduction assays were performed in duplicates and data are expressed as the means of two determinations. These data were subjected to statistic analysis using SigmaStat (Jandel Scientific Software, Guelph, Ont. Canada).

To examine the induction of RSV-specific CTL following DNA immunization, spleens from 2 immunized mice were removed to prepare single cell suspensions which were pooled. Splenocytes were incubated at $2.5 \times 10^6$ cells/mL in complete RPMI medium containing 10 U/mL murine interleukin 2 (IL-2) with γ-irradiated (3,000 rads) syngeneic splenocytes ($2.5 \times 10^6$ cells/mL) infected with 1 $TCID_{50}$/cell RSV (Long strain) for 2 hr. The source of murine IL-2 was supernatant of a mouse cell line constitutively secreting a high level of IL-2 obtained from Dr. R. Karasuyama of Basel Institute for Immunology (ref. 20). CTL activity was tested 5 days following the in vitro re-stimulation in a standard 4 hr chromium release assay. Target cells were 5 $^{51}$Cr-labelled uninfected BALB/c fibroblasts (BC cells) and persistently RSV-infected BCH14 fibroblasts, respectively. Washed responder cells were incubated with $2 \times 10^3$ target cells at varying effector to target ratios in 200 μL in 96-well V-bottomed tissue-culture plates for 4 hr at 37° C. Spontaneous and total chromium releases were determined by incubating target cells with either medium or 2.5% TRITON X-100 (a non-ionic surfactant) in the absence of responder lymphocytes. Percentage specific chromium release was calculated as (counts-spontaneous counts)/(total counts-spontaneous counts) X 100. Tests were performed in triplicates and data are expressed as the means of three determinations. For antibody blocking studies in CTL assays, the effector cells were incubated for 1 hr with 10 μg/ml final of purified mAb to CD4 (GK1.5) (ref. 21) or mAb against murine CD8 (53-6.7) (ref. 22) before adding chromium labelled BC or BCH4 cells. To determine the effect of anti-class I MHC antibodies on CTL killing, the chromium labelled target cells BC or BCH4 were incubated with 20 μL of culture supernate of hybridoma that secretes a mAb that recognizes $K^d$ and $D^d$ of class I MHC (34-1-2S) (ref. 23) prior to the addition of effector cells.

EXAMPLE 3

This Example describes the immunogenicity and protection by polynucleotide immunization by the intramuscular route.

To characterize the antibody responses following i.m. DNA administration, immune sera were analyzed for anti-RSV F IgG antibody titre by ELISA and for RSV-specific plaque reduction titre, respectively. All four plasmid constructs were found to be immunogenic. Sera obtained from mice immunized with pXL1–4 demonstrated significant anti-RSV F IgG titres and RSV-specific plaque reduction -titres as compared to the placebo group (Table 1 below) ($P<0.0061$ and $<0.0001$, respectively, Mann-Whitney Test). However, there is no significant difference in either anti-RSV F IgG titre or RSV-specific plaque reduction titre among mice immunized with either pXL1, pXL2, pXL3 or pXL4.

To evaluate the protective ability of pXL1–4 against primary RSV infection of the lower respiratory tract, immunized mice were challenged intranasally with mouse-adapted RSV and viral lung titres post challenge were assessed. All four plasmid constructs were found to protect animals against RSV infection. A significant reduction in the viral lung titre was observed in mice immunized with pXL1–4 as compared to the placebo group ($P<0.0001$, Mann-Whitney Test). However, varying degrees of protection were observed depending on the plasmid. In particular, PXL1 was more protective than pXL3 ($P=0.00109$, Mann-Whitney Test), and pXL4 more than pXL3 ($P=0.00125$), whereas only pXL2 induced complete protection. This conclusion was confirmed by another analysis with number of fully protected mice as end point (Fisher Exact Test). Constructs pXL1, pXL2 or pXL4 conferred a higher degree of protection than pXL3 ($P<0.004$, Fisher Exact Test) which was not more effective than placebo. Only pXL2 conferred full protection in all immunized mice.

The above statistical analysis revealed that PXL1 conferred more significant protection than pXL3. The former expresses the truncated and secretory form and the latter the intact membrane anchored form of the RSV F protein. Furthermore, pXL4 was shown to be more protective than pXL3. The difference between these two constructs is the presence of the intron II sequence in pXL4. Construct pXL2 which expresses the secretory form of the RSV-F in the context of the intron II sequence was the only plasmid that confers complete protection in all immunized mice.

EXAMPLE 4

This Example describes the influence of the route of administration of pXL2 on its immunogenicity and protective ability.

The i.m. and i.d. routes of DNA administration were compared for immunogenicity in terms of anti-RSV F antibody titres and RSV-specific plaque reduction titres. Analyses of the immune sera (Table 2 below) revealed that the i.d. route of DNA administration was as immunogenic as the i.m. route as judged by anti-RSV F IgG and IgG1 antibody responses as well as RSV-specific plaque reduction titres. However, only the i.m. route induced significant anti-RSV F IgG2a antibody responses, whereas the IgG2a isotype titre was negligible when the i.d. route was used. The i.m. and i.d. routes were also compared with respect to the induction of RSV-specific CTL. Significant RSV-specific CTL activity was detected in mice immunized intramuscularly. In contrast, the cellular response was significantly lower in mice inoculated intradermally (Table 3 below). In spite of these differences, protection against primary RSV infection of the lower respiratory tract was observed in both groups of mice immunized via either route (Table 4 below). The CTL induced by RSV-F DNA are classical CD8+ class I restricted CTL. The target cells, BCH4 fibroblasts express class I MHC only and do not express class II MHC. Further, prior incubation of BCH4 target cells with anti class-I MHC antibodies significantly blocked the lytic activity of RSV-F DNA induced CTL line. While anti-CD8 antibody could partially block lysis of BCH4 cells, antibody to CD4 molecule had no effect at all (Table 5 below). Lack of total blocking by mAb to CD8 could either be due to CTL being COB independent (meaning that even though they are CD8+ CTL, their TCR has enough affinity for class I MHC+peptide and it does not require CD8 interaction with the alpha 3 of class I MHC) or the amount of antibody used in these experiments was limiting. There was no detectable lysis of YAC-1 (NK sensitive target) cells (data not shown).

EXAMPLE 5

This Example describes immunization studies in cotton rats using pXL2.

The immune response of cotton rats to DNA immunization was analyzed by the protocol shown in Table 6 below. On day −5, 40 cotton rats were randomly selected and divided into 8 groups of 5. Cotton rats in groups 1 and 7 were inoculated intramuscularly (i.m.) into the tiberlia anteria (TA) muscles bilaterally with cardiotoxin (1.0 $\mu$M). On day −1, the cotton rats in group 8 were inoculated in the TA muscles with bupivacaine (0.25%). On day 0, several animals in each group were bled to determine levels of RSV-specific antibodies in the serum of the test animals prior to administration of vaccines. All of the animals were then inoculated i.m. or intradermally (i.d.) with 200 $\mu$g of plasmid DNA, placebo (non-RSV-specific DNA), 100 median cotton rat infectious doses (CRID50; positive control) of RSV, or of formalin inactivated RSV prepared in Hep-2 tissue culture cells and adjuvanted in alum. Forty-four days later the cotton rats in groups 1 & 7 were reinoculated with cardiotoxin in the TA muscles. Four days later (48 days after priming with vaccine), the animals in group 8 were reinoculated with bupivacains in the TA muscle of the right leg. The next day, (seven weeks after priming with vaccine) all of the animals were bled and all, except those in the group given live RSV, were boosted with the same material and doses used on day 0. 29 days later, each cotton rat was bled and then challenged intranasally (i.n.) with 100 CRID50 RSV A2 grown in Hep-2 tissue culture cells. Four days after this virus challenge (day +88) all of the cotton rats were killed and their lungs removed. One lobe from each set of lungs was fixed in formalin and then processed for histologic evaluation of pulmonary histopathology. The remaining lobes of lung will be assessed for the presence and levels of RSV. Each of the sera collected on days 0, 49 and 78 were tested for RSV-neutralizing activity, anti-RSV fusion activity and RSV-specific ELISA antibody.

The RSV neutralizing titres on day +49 and +78 are shown in Tables 7(a) below and 7(b) below respectively. As can be seen from the results shown in Table 7(a), on day +49 the animals immunized with live RSV and DNA immunization had substantial RSV serum neutralizing titres. The animals immunized with formalin-inactivated RSV had a neutralizing titre equivalent to the placebo group on day +49 but following boosting titres by day +78 had reached 5.8 ($\log_{10}/0.05$). Boosting had no significant effect upon animals immunized with live RSV or by i.m. plasmid immunization.

RSV titres in nasal washes (upper respiratory tract) on day +82 are shown in Table 8 below. RSV titres in the lungs (lower respiratory tract) on day +82 are shown in Table 9 below. All of the vaccines provided protection against lung infection but under these conditions, only live virus provided total protection against upper respiratory tract infection.

The lungs from the cotton rats were examined histologically for pulmonary histopathology and the results are shown in Table 10 below. With the exception of lung sections obtained from Group 9 which were essentially free of inflammatory cells or evidence of inflammation, and those from Group 3, which exhibited the maximal pulmonary pathology seen in this study, all of the sections of lung obtained from the other groups looked familiar, i.e. scattered inflammatory cells were present in most fields, and there was some thickening of septae. These are evidence of mild inflammatory diseases. Large numbers of inflammatory cells and other evidence of inflammation were present in- sections of lung from Group 3 (in which formalin-inactivated [FI] RSV vaccine was given prior to virus challenge). This result indicated that immunization with plasmid DNA expressing the RSV F protein does not result in pulmonary histopathology different from the placebo, whereas FI-RSV caused more severe pathology.

SUMMARY OF THE DISCLOSURE

In summary of this disclosure, the present invention provides certain novel vectors containing genes encoding an RSV F proteins, methods of immunization using such vectors and methods of diagnosis using such vectors. Modifications are possible within the scope of this invention.

TABLE 1

Immunogenic and Protective Abilities of pXL1–4 Mice via the i.m. Route

| Plasmid DNA Immunogen | No. Mice | Mean Anti-RSV F ELISA Titre (IgG)* ($Log_2$/100 ± SD) | Mean Plaque Reduction Titre* ($Log_4$ ± SD) | Post RSV Challenge Mean Virus Lung Titre# (pfu/g lung) ($Log_{10}$ ± SD) | No. Fully Protected Mice** |
|---|---|---|---|---|---|
| pXL1 | 8 | 3.00 ± 1.85 | 3.74 ± 0.98 | 0.72 ± 0.99 | 5 |
| pXL2 | 9 | 5.78 ± 1.72 | 4.82 ± 0.51 | 0.00 ± 0.00 | 9 |
| pXL3 | 8 | 3.75 ± 2.05 | 4.59 ± 1.16 | 2.77 ± 0.72 | 0 |
| pXL4 | 9 | 5.44 ± 1.13 | 5.18 ± 0.43 | 0.66 ± 1.00 | 6 |
| Placebo** | 12 | 0.58 ± 2.89 | 0.18 ± 0.62 | 3.92 ± 0.27 | 0 |

*These sets of data from sera obtained 1 week prior to the viral challenge
Detection sensitivity of the assay was $10^{1.96}$ pfu/g lung.
**The term, fully protected mice, refers to animals with no detectable RSV in lungs post challenge.

TABLE 2

Immunogenicity of pXL2 in Mice*

| Route | No. Mice | Mean Anti-RSV F ELISA Titre ($Log_2$/100 + SD) | | | Mean Plaque Reduction Titre ($Log_4$ ± SD) |
|---|---|---|---|---|---|
| | | IgG | IgG1 | IgG2a | |
| i.m | 8 | 7.63 ± 0.92 | 4.25 ± 1.91 | 4.38 ± 1.92 | 4.18 ± 0.88 |
| i.d. | 7 | 7.00 ± 1.00 | 5.00 ± 1.00 | 0.14 ± 0.38 | 3.65 ± 0.59 |
| Placebo (i.m.) | 9 | 0.50 ± 0.51 | 0.00 ± 0.00 | 0.00 ± 0.00 | 0.18 ± 0.50 |

*These sets of data are from sera obtained 1 week prior to the viral challenge.

TABLE 3

Induction of RSV-specific CTL Following DNA Immunization*

| Route | E:T Ratio | % Specific Lysis BC | % Specific Lysis BCH4 |
|---|---|---|---|
| i.m. | 200:1 | 23.3 | 100.6 |
| | 100:1 | 17.0 | 62.4 |
| | 50:1 | 19.9 | 64.1 |
| | 25:1 | 22.3 | 46.4 |
| i.d. | 100:1 | 20.9 | 26.1 |
| | 50:1 | 21.7 | 19.1 |
| | 25:1 | 7.1 | 7.0 |
| | 12.5:1 | 2.8 | 2.3 |

*These set of data were obtained from immunized mice immediately prior to RSV challenge.

TABLE 4

Immunoprotective Ability of pXL2 in Mice

| Route | No. Mice | Post RSV Challenge Mean Virus Lung Titre* (pfu/g lung) | No. Fully Protected Mice# |
|---|---|---|---|
| i.m. | 8 | 0.00 ± 0.00 | 8 |
| i.d. | 7 | 0.43 ± 1.13 | 6 |
| Placebo (i.m.) | 9 | 4.30 ± 022 | 0 |

*Detection sensitivity of the assay was $10^{1.69}$ pfu/g lung.
The term, fully protected mice, refers to animals with no detectable RSV in lungs post challenge.

TABLE 5

RSV specific CTL included by i.m. DNA immunization are class I restricted CTL

| E:T Ratio | BCH4 | BCH4 + anti-CD4 | BCH4 + anti-CD8 | BCH4 + anti-class I MHC |
|---|---|---|---|---|
| 100:1 | 52.03 | 54.3 | 39.4 | 8.6 |
| 50:1 | 44.4 | 47.2 | 27.4 | 6.2 |

TABLE 5-continued

RSV specific CTL included by i.m. DNA immunization are class I restricted CTL

| E:T Ratio | BCH4 | BCH4 + anti-CD4 | BCH4 + anti-CD8 | BCH4 + anti-class I MHC |
|---|---|---|---|---|
| 25:1 | 28.6 | 26.3 | 14.8 | 1 |
| 12.5:1 | 18.2 | 15 | 8 | −2.7 |

TABLE 6

| Group | Antigen | RSV-specific dose | Inoc. route | Pretreatment/ Adjuvant | Day 0 | Day 49 | Day 78 | Day 88 |
|---|---|---|---|---|---|---|---|---|
| 1 | Placebo | 0 | I.M. | Cardiotoxin | Prebleed, several cotton rats per group; prime all animals | Bleed all animals; boost all except those in group 2 | Challenge with RSV A2 I.N. after bleeding all | Harv. animals and do histologic evaluation, pulmonary virus titers, antibodies |
| 2 | Live RSV | 100 CRID50 | I.N. | None | | | | |
| 3 | FI-RSV | | I.M. | Alum | | | | |
| 5 | pXL2 | 200 μg | I.M. | None | | | | |
| 6 | pXL2 | 200 μg | I.D. | None | | | | |
| 7 | pXL2 | 200 μg | I.M. | Cardiotoxin | | | | |
| 8 | pXL2 | 200 μg | I.M. | Bupivacaine | | | | |

TABLE 7(a)

RSV Serum Neutralizing Titers on Day 49

| Group | Antigen | RSV-specific dose | Inoc. route | Nt. antibody titer ($log_2$/0.05 ml) in CR no. 1 | 2 | 3 | 4 | Mean titer $log_2$/0.05 | Stand. Dev. |
|---|---|---|---|---|---|---|---|---|---|
| 1 | Placebo | 0 | I.M. | 4 | 3 | 2 | 2 | 2.75 | 1.0 |
| 2 | Live RSV | 100 CRID50 | I.N. | 9 | 9 | 9 | 9 | 9 | 0.0 |
| 3 | FI-RSV | | I.M. | 0 | 4 | 2 | 2 | 2.0 | 1.6 |
| 5 | pXL2 | 200 μg | I.M. | 9 | 8 | 8 | 7 | 8.0 | 0.8 |
| 6 | pXL2 | 200 μg | I.D. | 5 | 2 | 5 | 5 | 4.3 | 1.5 |
| 7 | pXL2 | 200 μg | I.M. | 8 | 8 | 9 | 9 | 8.5 | 0.6 |
| 8 | pXL2 | 200 μg | I.M. | 8 | 9 | 6 | 6 | 7.3 | 1.5 |

TABLE 7(b)

RSV Serum Neutralizing Titers on Day 78

| Group | Antigen | RSV-specific dose | Inoc. route | Nt. antibody titer ($log_2$/0.05 ml) in CR no. 1 | 2 | 3 | 4 | Mean titer $log_2$/0.05 | Stand. Dev. |
|---|---|---|---|---|---|---|---|---|---|
| 1 | Placebo | 0 | I.M. | 3 | 2 | 4 | Died | 3.0 | 1.0 |
| 2 | Live RSV | 100 CRID50 | I.N. | 8 | 9 | 8 | 9 | 8.5 | 0.6 |
| 3 | FI-RSV | | I.M. | 8 | 4 | 6 | 5 | 5.8 | 1.7 |
| 5 | pXL2 | 200 μg | I.M. | 7 | 8 | 8 | 8 | 7.8 | 0.5 |
| 6 | pXL2 | 200 μg | I.D. | 8 | 6 | 6 | Died | 6.7 | 1.2 |
| 7 | PXL2 | 200 μg | I.M. | 8 | 9 | 9 | 8 | 8.7 | 0.6 |
| 8 | pXL2 | 200 μg | I.M. | 8 | 7 | 9 | 9 | 8.3 | 1.0 |

TABLE 8

RSV Titers in Nasal Washes on Day 82

| Group | Antigen | RSV-specific dose | Inoc. route | RSV titer ($\log_{10}$/0.05 ml) in cotton rat no. 1 | 2 | 3 | 4 | Mean titer $\log_{10}$/0.05 | Stand. Dev. |
|---|---|---|---|---|---|---|---|---|---|
| 1 | Placebo | 0 | I.M. | 3.4 | 3.3 | 3.3 | Died | 3.3 | 0.1 |
| 2 | Live RSV | 100 CRID50 | I.N. | 0 | 0 | 0 | 0 | 0.0 | 0.0 |
| 3 | FI-RSV | | I.M. | 0 | 0 | 2.8 | 0 | 0.7 | 1.4 |
| 5 | pXL2 | 200 µg | I.M. | 3.3 | 2.3 | 3.3 | 2.3 | 2.8 | 0.6 |
| 6 | pXL2 | 200 µg | I.D. | N.D. | N.D. | N.D. | Died | N.D. | N.D. |
| 7 | pXL2 | 200 µg | I.M. | 2.3 | 0 | 0 | 3.2 | 1.4 | 1.6 |
| 8 | pXL2 | 200 µg | I.M. | N.D. | N.D. | N.D. | N.D. | N.D. | N.D. |

N.D. = non-determined

TABLE 9

Titers in Lungs on Day 82

| Group | Antigen | RSV-specific dose | Inoc. route | RSV titer ($\log_{10}$/g lung) in cotton rat no. 1 | 2 | 3 | 4 | Mean titer $\log_{10}$/0.05 | Stand. Dev. |
|---|---|---|---|---|---|---|---|---|---|
| 1 | Placebo | 0 | I.M. | 4.7 | 4.2 | 3.7 | Died | 4.2 | 0.5 |
| 2 | Live RSV | 100 CRID50 | I.N. | 0 | 0 | 0 | 0 | 0.0 | 0.0 |
| 3 | FI-RSV | $10^5$ PFU | I.M. | 0 | 0 | 0 | 0 | 0.0 | 0.0 |
| 5 | pXL2 | 200 µg | I.M. | 0 | 2.2 | 0 | 0 | 0.6 | 1.1 |
| 6 | pXL2 | 200 µg | I.D. | 0 | 2.2 | 2.7 | 3.2 | 2.0 | N.D. |
| 7 | pXL2 | 200 µg | I.M. | 0 | 0 | 0 | 0 | 0.0 | 0.0 |
| 8 | pXL2 | 200 µg | I.M. | 0 | 0 | 0 | 0 | 0.0 | N.D. |

N.D. = non-determined

TABLE 10

Summary of Histopathology Results Seen in Sections of Cotton Rat Lung

| Group | Treatment | Major Observations & Comments |
|---|---|---|
| 1. | Placebo + RSV | Scattered individual and groups of macrophages and polymorphonuclear neutrophiles (PMN) in all fields. Overt thickening of septae. Occasional pyknotic cells seen. Overall: mild to moderate inflammation. |
| 2. | Live RSV | Isolated macrophages seen in most fields. Scattered PMN. Overall: minimal inflammation. |
| 3. | FI-RSV + RSV | Virtually every field contains numerous mononuclear cells & PMN. Pyknotic cells and debris common. Thickened septae. Evidence of exacerbated disease. |
| 5. | Plasmid + RSV | Isolated macrophages seen in most fields. Occasional PMN seen. Very similar to live virus group. |
| 6. | Plasmid i.d. + RSV | Isolated macrophages seen in most fields. Occasional PMN seen. |
| 7. | Plasmid + CT + RSV | Isolated mononuclear cells and PMN seen in most fields. |
| 8. | Plasmid + Biv + RSV | Scattered mononuclear cells and PMN seen in most fields. |
| 9. | Normal CR Lung | Few leukocytes evidence. Airy, open appearance. Thin septae. |

CT = carditoxin
Biv = bupivacaine

REFERENCES

1. McIntosh K., Canock, R. M. In: Fields B N, Knipe, D M, editors. Virology. New York: Raven Press: 1990: 1045–1072

2. Katz S L., In: New Vaccine Development establishing priorities. Vol. 1. Washington: National Academic Press: 1985: 397–409.

3. Wertz G W, Sullender W M., Biotechnology 1992; 20: 151–176

4. Johnson et al., J. Virol 1987, 61: 3163–3166

5. Pemberton et al., J. Gen Virol. 1987, 68: 2177–2182

6. Crowe, J. E., Vaccine 1995, 13: 415–421

7. WO 90/11092

8. WO 94/21797

9. Ulmer, Current Opinion, Invest Drugs, 1993, 2: 983–989

10. Tang et al., Nature 1992, 356: 152–154

11. Furth et al. Analytical Biochemistry, 1992, 205: 365–368

12. Pizzorno et al., J. Virol. 1988, 62: 1167–1179

13. Chapman, B. S.; Thayer, R. M.; Vincent, K. A. and Haigwood, N. L., Nucl. Acids. Res. 1991, 19: 3979–3986.

14. Green, S. Isseman, I., and Sheer, E., Nucl. Acids. Res. 1988, 16: 369

15. Breathnack, R. and Harris, B. A., Nucl. Acids Res. 1983, 11: 7119–7136

16. Graham, B. S.; Perkins M. D.; Wright, P. F. and Karzon, D. T. J. Mod. Virol. 1988 26: 153–162.

17. Nabel, G. J. 1993, Proc. Natl. Acad. Sci. USA 90: 11307–11311.

18. Du, R. P et al. 1994., Biotechnology 12: 813–818.

19. Prince, G. A. et al, 1978. Ame. J. Pathol. 93: 771–790.

20. Karasuyama & Melchers, Eur. J. Immunol. 18, 97–104, 1988

21. Wilde David B., et al. 1983 J. Immunol. 131: 2178–2183.

22. Ledbetter, J. A., Rouse R., Micklem, H. 1980, J. Exp. Med. 152: 280–295.

23. Ozato Keiko, et al, 1982, Transplantation 34: 113–118.

24. Davis et al., Vaccine 1994, 12: 1503–1509.

What we claim is:

1. A method of immunizing a host against disease caused by infection with respiratory syncytial virus (RSV), which comprises administering to said host an effective amount of a plasmid vector comprising:
   a first nucleotide sequence encoding an RSV F protein that generates antibodies, said first nucleotide sequence being selected from the group consisting of:
   a nucleotide sequence having SEQ ID NO:1,
   a nucleotide sequence having SEQ ID NO:3,
   a nucleotide sequence encoding an amino acid sequence having SEQ ID NO:2, and
   a nucleotide sequence encoding an amino acid sequence having SEQ ID NO:4,
   a promoter sequence operatively coupled to said first nucleotide sequence for expression of said RSV F protein in said host, and
   a second nucleotide sequence located between said first nucleotide sequence and said promoter sequence and comprising a pair of splice sites to prevent aberrant mRNA splicing and to increase expression of said RSV F protein when expressed in vivo from said vector in said host.

2. The method of claim 1 wherein said host is a human.

3. The method of claim 1 wherein said first nucleotide sequence encodes a full-length RSV F protein having the sequence of SEQ ID NO:2.

4. The method of claim 1 wherein said first nucleotide sequence encodes an RSV F protein from which the transmembrane region is absent and having the sequence of SEQ ID NO:4.

5. The method of claim 1 wherein said promoter sequence is an immediate early cytomegalovirus promoter.

6. The method of claim 1 wherein said second nucleotide sequence is that of rabbit β-globin intron II.

7. The method of claim 2 wherein said promoter sequence is an immediate early cytomegalovirus promoter.

8. A method of using a gene encoding an RSV F protein that generates antibodies to produce an immune response in a host, which comprises:
   isolating said gene, said gene having a nucleotide sequence being selected from the group consisting of:
   a nucleotide sequence having SEQ ID NO:1,
   a nucleotide sequence having SEQ ID NO:3,
   a nucleotide sequence encoding an amino acid sequence having SEQ ID NO:2, and
   a nucleotide sequence encoding an amino acid sequence having SEQ ID NO:4;
   operatively linking said gene to a promoter sequence to produce a plasmid vector, said promoter sequence directing expression of said RSV F protein when said vector is introduced into a host to produce an immune response to said RSV F protein;
   operatively linking said gene in said plasmid vector to a nucleotide sequence comprising a pair of splice sites to prevent aberrant mRNA splicing and to increase expression of said RSV F protein in said host, and
   introducing said non-replicating vector into the host.

9. The method of claim 8 wherein said gene encoding an RSV F protein encodes an RSV F protein lacking the transmembrane region.

10. The method of claim 8 wherein said nucleotide sequence is introduced into said vector between said promoter sequence and said gene.

11. The method of claim 9 wherein said promoter sequence comprises the immediate early cytomegalovirus promoter.

12. The method of claim 10 wherein said nucleotide sequence is that of rabbit β-globin intron II.

13. A method of producing a vaccine for protection of a host against disease caused by infection with respiratory syncytial virus (RSV), which comprises:
   isolating a first nucleotide sequence encoding an RSV F protein that generates antibodies, said first nucleotide sequence being selected from the group consisting of:
   a nucleotide sequence having SEQ ID NO:1,
   a nucleotide sequence having SEQ ID NO:3,
   a nucleotide sequence encoding an amino acid sequence having SEQ ID NO:2, and
   a nucleotide sequence encoding an amino acid sequence having SEQ ID NO:4;
   operatively linking said first nucleotide sequence to a promoter sequence to produce a plasmid vector, the promoter sequence directing expression of said RSV F protein when introduced into a host to produce an immune response to said RSV F protein;
   operatively linking said first nucleotide sequence to a second nucleotide sequence between said first nucleotide sequence and said promoter sequence in said vector, said second nucleotide sequence comprising a pair of splice sites to prevent aberrant mRNA splicing and to increase expression of said RSV F protein when expressed in vivo from the vector in a host, and
   formulating said plasmid vector as a vaccine for in vivo administration.

14. A vaccine produced by the method of claim 13.

15. The method of claim 13 wherein said vector is selected from group consisting of pXL1 and pXL2.

16. The method of claim 13 wherein said first nucleotide sequence encodes a full-length RSV F protein having an amino acid sequence having SEQ ID NO:2.

17. The method of claim 13 wherein said first nucleotide sequence encodes a RSV F protein from which the transmembrane region is absent and having an amino acid sequence having SEQ ID NO:4.

18. A method of producing a vaccine for protection of a host against disease caused by infection with respiratory syncytial virus (RSV), which comprises:
   isolating a nucleotide sequence encoding an RSV F protein from which the transmembrane region is absent, said nucleotide sequence having SEQ ID NO:3 or encoding an RSV F protein having the amino acid sequence having SEQ ID NO:4;
   operatively linking said nucleotide sequence to a promoter sequence to produce a plasmid vector, the promoter sequence directing expression of said RSV F protein when introduced into a host to produce an immune response to said RSV F protein; and
   formulating said vector as a vaccine for in vivo administration.

19. A vaccine produced by the method of claim 18.

20. A plasmid vector, comprising:
   a first nucleotide sequence encoding a truncated RSV F protein lacking a transmembrane region,
   a promoter sequence operatively coupled to said nucleotide sequence for expression of said truncated RSV F protein, and
   a second nucleotide sequence comprising a pair of splice sites to prevent aberrant mRNA splicing.

21. The vector of claim 20, wherein said promoter sequence is an immediate early cytomegalovirus promoter.

22. The vector of claim 20 wherein said first nucleotide sequence has SEQ ID NO:3.

23. The vector of claim 20 wherein said first nucleotide sequence encodes a truncated RSV F protein having an amino acid sequence of SEQ ID NO:4.

24. The vector of claim 20 wherein said further nucleotide sequence is located between said first nucleotide sequence and said promoter sequence.

25. The vector of claim 20 which is plasmid pXL2 as shown In FIG. 5.

26. The vector of claim 20 which is plasmid pXL4 as shown in FIG. 7.

27. The vector of claim 24 wherein said further nucleotide sequence is that of rabbit β-globin intron II.

28. A method of immunizing a host against disease caused by infection with respiratory syncytial virus (RSV), which comprises administering to said host an effective amount of a plasmid vector comprising a nucleotide sequence having SEQ ID NO:3 or encoding a truncated RSV F protein lacking a transmembrane region and having SEQ ID NO:4, and a promoter sequence operatively coupled to said nucleotide sequence for expression of said truncated RSV F protein in said host.

29. The method of claim 28 wherein said host is a human.

30. The method of claim 29 wherein said promoter sequence is an immediately early cytomegalovirus promoter.

31. The method of claim 29 wherein said vector further comprises a further nucleotide sequence comprising a pair of splice sites to prevent mRNA splicing.

32. The method of claim 29 wherein said vector is selected from the group consisting of plasmid pXL2 as shown in FIG. 5 and plasmid pXL4 as shown in FIG. 7.

33. The method of claim 31 wherein said further nucleotide sequence is located between said nucleotide sequence and said promoter sequence.

34. The method of claim 33 wherein said further nucleotide sequence is that of rabbit β-globin intron II.

35. A method of using a nucleotide sequence encoding a truncated RSV F protein lacking a transmembrane region to produce an immune response in a host, which comprises:
   isolating said nucleotide sequence,
   operatively linking said nucleotide expression to a promoter sequence to produce a plasmid vector wherein said promoter sequence directs expression of said truncated RSV F protein when said vector is introduced into a host to produce an immune response to said truncated RSV F protein; and
   introducing said plasmid vector into the host.

36. The method of claim 35 wherein said host is a human host.

37. The method of claim 36 wherein said promoter sequence is an immediate early cytomegalovirus promoter.

38. The method of claim 36 wherein said nucleotide sequence has SEQ ID NO:3.

39. The method of claim 36 wherein said nucleotide sequence encodes a truncated RSV F protein having an amino acid sequence of SEQ ID NO:4.

40. The method of claim 36 wherein said vector further comprises a further nucleotide sequence comprising a pair of splice sites to prevent aberrant mRNA splicing.

41. The method of claim 36 wherein said plasmid vector is plasmid pXL2 shown in FIG. 5.

42. The method of claim 36 wherein said plasmid vector is plasmid pXL4 shown in FIG. 7.

43. The method of claim 40 wherein said further nucleotide sequence is located between said nucleotide sequence and said promoter sequence.

44. The method of claim 43 wherein said further nucleotide sequence is that of rabbit β-globin intron II.

* * * * *

SEQUENCE LISTING

<160> NUMBER OF SEQ ID NOS: 5

<210> SEQ ID NO 1
<211> LENGTH: 1886
<212> TYPE: DNA
<213> ORGANISM: respiratory syncytial virus

<400> SEQUENCE: 1

```
atggagttgc caatcctcaa agcaaatgca attaccacaa tcctcgctgc agtcacattt      60
tgctttgctt ctagtcaaaa catcactgaa gaattttatc aatcaacatg cagtgcagtt     120
agcaaaggct atcttagtgc tctaagaact ggttggtata ctagtgttat aactatagaa     180
ttaagtaata tcaaggaaaa taagtgtaat ggaacagatg ctaaggtaaa attgatgaaa     240
caagaattag ataaatataa aaatgctgta acagaattgc agttgctcat gcaaagcaca     300
ccagcagcaa caatcgagc cagaagagaa ctaccaaggt ttatgaatta tacactcaac     360
aataccaaaa aaaccaatgt aacattaagc aagaaaagga aagaagatt tcttggtttt     420
ttgttaggtg ttggatctgc aatcgccagt ggcattgctg tatctaaggt cctgcactta     480
gaaggagaag tgaacaagat caaaagtgct ctactatcca caaacaaggc cgtagtcagc     540
ttatcaaatg gagttagtgt cttaaccagc aaagtgttag acctcaaaaa ctatatagat     600
aaacaattgt tacctattgt gaataagcaa agctgcagaa tatcaaatat agaaactgtg     660
atagagttcc aacaaaagaa caacagacta ctagagatta ccagggaatt tagtgttaat     720
gcaggtgtaa ctacacctgt aagcacttac atgttaacta atagtgaatt attgtcatta     780
atcaatgata tgcctataac aaatgatcag aaaaagttaa tgtccaacaa tgttcaaata     840
gttagacagc aaagttactc tatcatgtcc ataataaaag aggaagtctt agcatatgta     900
gtacaattac cactatatgg tgtgatagat acaccttgtt ggaaattaca cacatcccct     960
ctatgtacaa ccaacacaaa agaagggtca aacatctgtt taacaagaac tgacagagga    1020
tggtactgtg acaatgcagg atcagtatct ttcttcccac aagctgaaac atgtaaagtt    1080
caatcgaatc gagtattttg tgacacaatg aacagtttaa cattaccaag tgaagtaaat    1140
ctctgcaatg ttgacatatt caatcccaaa tatgattgta aaattatgac ttcaaaaaca    1200
gatgtaagca gctccgttat cacatctcta ggagccattg tgtcatgcta tggcaaaact    1260
aaatgtacag catccaataa aaatcgtgga atcataaaga cattttctaa cgggtgtgat    1320
tatgtatcaa ataaggggt ggacactgtg tctgtaggta acacattata ttatgtaaat    1380
aagcaagaag gcaaaagtct ctatgtaaaa ggtgaaccaa taataaattt ctatgacccca   1440
ttagtattcc cctctgatga atttgatgca tcaatatctc aagtcaatga aagattaac    1500
cagagtttag catttattcg taaatccgat gaattattac ataatgtaaa tgctggtaaa    1560
tcaaccacaa atatcatgat aactactata attatagtga ttatagtaat attgttatca    1620
ttaattgctg ttggactgct cctatactgt aaggccagaa gcacaccagt cacactaagc    1680
aaggatcaac tgagtggtat aaataatatt gcatttagta actgaataaa aatagcacct    1740
aatcatgttc ttacaatggt ttactatctg ctcatagaca acccatctat cattggattt    1800
tcttaaaatc tgaacttcat cgaaactctt atctataaac catctcactt acactattta    1860
```
agtagattcc tagtttatag ttatat                                             1886

<210> SEQ ID NO 2
<211> LENGTH: 594
<212> TYPE: PRT
<213> ORGANISM: respiratory syncytial virus

<400> SEQUENCE: 2

Met Glu Leu Pro Ile Leu Lys Ala Asn Ala Ile Thr Thr Ile Leu Ala
 1               5                  10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Met Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Arg Ser Cys Arg Ile Ser Asn Ile Glu Thr Val Ile Glu Phe Gln
    210                 215                 220

His Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

```
Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Leu Val Phe Pro Ser Asp Glu Phe Asp Ala Ser Ile
            500                 505                 510

Ser Gln Val Asn Glu Lys Ile Asn Gln Ser Leu Ala Phe Ile Arg Lys
            515                 520                 525

Ser Asp Glu Leu Leu His Asn Val Asn Ala Gly Lys Ser Thr Thr Asn
    530                 535                 540

Ile Met Ile Thr Thr Ile Ile Ile Glu Ile Ile Val Ile Leu Leu Ser
545                 550                 555                 560

Leu Ile Ala Val Gly Leu Leu Leu Tyr Cys Lys Ala Arg Ser Thr Pro
                565                 570                 575

Val Thr Leu Ser Lys Asp Gln Leu Ser Gly Ile Asn Asn Ile Ala Phe
                580                 585                 590

Ser Asn

<210> SEQ ID NO 3
<211> LENGTH: 1904
<212> TYPE: DNA
<213> ORGANISM: respiratory syncytial virus

<400> SEQUENCE: 3
atggagttgc caatcctcaa agcaaatgca attaccacaa tcctcgctgc agtcacattt     60
tgctttgctt ctagtcaaaa catcactgaa gaattttatc aatcaacatg cagtgcagtt    120
agcaaaggct atcttagtgc tctaagaact ggttggtata ctagtgttat aactatagaa    180
ttaagtaata tcaaggaaaa taagtgtaat ggaacagatg ctaaggtaaa attgatgaaa    240
caagaattag ataaatataa aaatgctgta acagaattgc agttgctcat gcaaagcaca    300
ccagcagcaa caatcgagc cagaagagaa ctaccaaggt ttatgaatta cactctcaac    360
aataccaaaa aaaccaatgt aacattaagc aagaaaagga aagaagatt tcttggtttt    420 ttgttaggtg ttggatctgc aatcgccagt ggcattgctg tatctaaggt cctgcactta    480
gaaggagaag tgaacaagat caaaagtgct ctactatcca aaacaaggc cgtagtcagc    540 ttatcaaatg gagttagtgt cttaaccagc aaagtgttag acctcaaaaa ctatatagat    600
aaacaattgt tacctattgt gaataagcaa agctgcagaa tatcaaatat agaaactgtg    660
atagagttcc aacaaaagaa caacagacta ctagagatta ccaggaatt tagtgttaat    720 gcaggtgtaa ctacacctgt aagcacttac atgttaacta atagtgaatt attgtcatta    780
```

-continued

```
atcaatgata tgcctataac aaatgatcag aaaaagttaa tgtccaacaa tgttcaaata      840
gttagacagc aaagttactc tatcatgtcc ataataaaag aggaagtctt agcatatgta      900
gtacaattac cactatatgg tgtgatagat acaccttgtt ggaaattaca cacatcccct     960
ctatgtacaa ccaacacaaa agaagggtca acatctgtt taacaagaac tgacagagga     1020
tggtactgtg acaatgcagg atcagtatct ttcttcccac aagctgaaac atgtaaagtt     1080
caatcgaatc gagtattttg tgacacaatg aacagtttaa cattaccaag tgaagtaaat     1140
ctctgcaatg ttgacatatt caatcccaaa tatgattgta aaattatgac ttcaaaaaca     1200
gatgtaagca gctccgttat cacatctcta ggagccattg tgtcatgcta tggcaaaact     1260
aaatgtacag catccaataa aaatcgtgga atcataaaga cattttctaa cgggtgtgat     1320
tatgtatcaa ataaaggggt ggacactgtg tctgtaggta acacattata ttatgtaaat     1380
aagcaagaag gcaaaagtct ctatgtaaaa ggtgaaccaa taataaattt ctatgaccca     1440
ttagtattcc cctctgatga atttgatgca tcaatatctc aagtcaatga gaagattaac     1500
cagagtttag catttattcg taaatccgat gaattattac ataatgtaaa tgctggtaaa     1560
tcaaccacaa atatcatgac ttgataatga ggatccataa ctactataat tatagtgatt     1620
atagtaatat tgttatcatt aattgctgtt ggactgctcc tatactgtaa ggccagaagc     1680
acaccagtca cactaagcaa ggatcaactg agtggtataa ataatattgc atttagtaac     1740
tgaataaaaa tagcacctaa tcatgttctt acaatggttt actatctgct catagacaac     1800
ccatctatca ttggatttttc ttaaaatctg aacttcatcg aaactcttat ctataaacca     1860
tctcacttac actatttaag tagattccta gtttatagtt atat                     1904
```

<210> SEQ ID NO 4
<211> LENGTH: 527
<212> TYPE: PRT
<213> ORGANISM: respiratory syncytial virus

<400> SEQUENCE: 4

```
Met Glu Leu Pro Ile Leu Lys Ala Asn Ala Ile Thr Thr Ile Leu Ala
 1               5                  10                  15

Ala Val Thr Phe Cys Phe Ala Ser Ser Gln Asn Ile Thr Glu Glu Phe
             20                  25                  30

Tyr Gln Ser Thr Cys Ser Ala Val Ser Lys Gly Tyr Leu Ser Ala Leu
         35                  40                  45

Arg Thr Gly Trp Tyr Thr Ser Val Ile Thr Ile Glu Leu Ser Asn Ile
     50                  55                  60

Lys Glu Asn Lys Cys Asn Gly Thr Asp Ala Lys Val Lys Leu Met Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175
```

Ala Val Val Ser Leu Ser Asn Gly Val Ser Val Leu Thr Ser Lys Val
                180                 185                 190

Leu Asp Leu Lys Asn Tyr Ile Asp Lys Gln Leu Leu Pro Ile Val Asn
            195                 200                 205

Lys Gln Ser Cys Arg Ile Ser Asn Ile Glu Thr Val Ile Glu Phe Gln
        210                 215                 220

His Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
        290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
        370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Thr
        515                 520                 525

<210> SEQ ID NO 5
<211> LENGTH: 573
<212> TYPE: DNA
<213> ORGANISM: respiratory syncytial virus

<400> SEQUENCE: 5
gtgagtttgg ggaccttga ttgttctttc ttttcgcta ttgtaaaatt catgttatat     60 ggaggggca aagttttcag ggtgttgttt agaatggaa gatgtccctt gtatcaccat    120
ggaccctcat gataatttg tttctttcac tttctactct gttgacaacc attgtctcct    180

-continued

```
cttatttct   tttcattttc  tgtaactttt  tcgttaaact  ttagcttgca  tttgtaacga    240
atttttaaat  tcacttttgt  ttatttgtca  gattgtaagt  actttctcta  atcacttttt    300
tttcaaggca  atcagggtat  attatattgt  acttcagcac  agtttttagag aacaattgtt    360 ataattaaat  gataaggtag  aatatttctg  catataaatt  ctggctggcg  tggaaatatt    420
cttattggta  gaaacaacta  catcctggtc  atcatcctgc  ctttctcttt  atggttacaa    480
tgatatacac  tgtttgagat  gaggataaaa  tactctgagt  ccaaaccggg  ccctctgct     540 aaccatgttc  atgccttctt  cttttccta   cag                                   573
```